(12) United States Patent
Foo et al.

(10) Patent No.: US 10,377,893 B2
(45) Date of Patent: Aug. 13, 2019

(54) ELASTOMERIC FILM-FORMING COMPOSITIONS AND ARTICLES MADE FROM THE ELASTOMERIC FILM

(71) Applicant: SKINPROTECT CORPORATION SDN BHD, Klang, Selangor (MY)

(72) Inventors: Khon Pu Foo, Selangor (MY); Kumaresan Prabhakaran, Selangor (MY)

(73) Assignee: SKINPROTECT CORPORATION SDN BHD, Klang, Selangor (MY)

( * ) Notice: Subject to any disclaimer, the term of this patent is extended or adjusted under 35 U.S.C. 154(b) by 543 days.

(21) Appl. No.: 14/905,644

(22) PCT Filed: Jul. 16, 2014

(86) PCT No.: PCT/AU2014/000727
§ 371 (c)(1),
(2) Date: Jan. 15, 2016

(87) PCT Pub. No.: WO2015/006808
PCT Pub. Date: Jan. 22, 2015

(65) Prior Publication Data
US 2016/0159992 A1 Jun. 9, 2016

(30) Foreign Application Priority Data

Jul. 16, 2013 (AU) .................. 2013902628

(51) Int. Cl.
*A41D 19/00* (2006.01)
*C08L 47/00* (2006.01)
(Continued)

(52) U.S. Cl.
CPC .......... *C08L 47/00* (2013.01); *A41D 19/0062* (2013.01); *A41D 19/0082* (2013.01);
(Continued)

(58) Field of Classification Search
CPC .... A41D 19/0062; A41D 19/04; A41D 19/02; C08J 7/047; C08J 7/14
See application file for complete search history.

(56) References Cited

U.S. PATENT DOCUMENTS 2,385,182 A 9/1945 Anderson et al.
2,868,754 A 1/1959 Eilbeck et al.
(Continued)

FOREIGN PATENT DOCUMENTS

CA 2032094 A1 6/1991
CN 103724543 A 4/2014
(Continued)

OTHER PUBLICATIONS

Datta, R.N., "Rubber Curing Systems", Rapra Review Reports, Report 144, vol. 12, No. 12 (2002) (in English; 157 pages).
(Continued)

*Primary Examiner* — Tajash D Patel
(74) *Attorney, Agent, or Firm* — Westerman, Hattori, Daniels & Adrian, LLP

(57) ABSTRACT

The invention relates to an elastomeric film-forming composition comprising a carboxylic acid- or ester-grafted polychlorobutadiene, and one or more cross-linking agents. The invention also relates to dipped articles, gloves, methods of manufacture and uses involving the composition.

37 Claims, 2 Drawing Sheets

(51) Int. Cl.

| | | |
|---|---|---|
| B29C 41/14 | (2006.01) | |
| C08J 3/26 | (2006.01) | |
| C08J 3/24 | (2006.01) | |
| C08J 5/02 | (2006.01) | |
| A61B 42/00 | (2016.01) | |
| B05D 1/18 | (2006.01) | |
| C09D 151/04 | (2006.01) | |
| C08K 3/22 | (2006.01) | |
| C08K 3/30 | (2006.01) | |
| C08L 9/04 | (2006.01) | |
| C08C 19/28 | (2006.01) | |
| C08L 9/02 | (2006.01) | |
| C08L 15/00 | (2006.01) | |
| C08L 51/04 | (2006.01) | |
| C08K 3/011 | (2018.01) | |
| C08J 5/18 | (2006.01) | |
| B29K 19/00 | (2006.01) | |
| C08F 236/18 | (2006.01) | |
| C08L 13/02 | (2006.01) | |
| A61B 17/00 | (2006.01) | |
| B29L 31/48 | (2006.01) | |

(52) U.S. Cl.
CPC ............ *A61B 42/00* (2016.02); *B05D 1/18* (2013.01); *B29C 41/14* (2013.01); *C08C 19/28* (2013.01); *C08J 3/24* (2013.01); *C08J 3/243* (2013.01); *C08J 3/26* (2013.01); *C08J 5/02* (2013.01); *C08J 5/18* (2013.01); *C08K 3/011* (2018.01); *C08K 3/22* (2013.01); *C08K 3/30* (2013.01); *C08L 9/02* (2013.01); *C08L 9/04* (2013.01); *C08L 15/00* (2013.01); *C08L 51/04* (2013.01); *C09D 151/04* (2013.01); *A61B 2017/00889* (2013.01); *B29K 2019/00* (2013.01); *B29L 2031/4864* (2013.01); *C08F 236/18* (2013.01); *C08J 2309/04* (2013.01); *C08J 2309/10* (2013.01); *C08J 2311/00* (2013.01); *C08J 2347/00* (2013.01); *C08J 2409/04* (2013.01); *C08J 2409/10* (2013.01); *C08J 2423/22* (2013.01); *C08L 13/02* (2013.01)

(56) References Cited

U.S. PATENT DOCUMENTS

| | | | |
|---|---|---|---|
| 3,286,011 | A | 11/1966 | Kavalir et al. |
| 3,920,600 | A | 11/1975 | Ahramjian |
| 3,937,659 | A | 2/1976 | Boldt et al. |
| 3,943,193 | A | 3/1976 | Miyagawa et al. |
| 3,988,506 | A | 10/1976 | Dohi et al. |
| 4,116,743 | A | 9/1978 | Davis |
| 4,130,528 | A | 12/1978 | Chen |
| 4,141,875 | A | 2/1979 | Brizzolara et al. |
| 4,205,559 | A | 6/1980 | Long et al. |
| 4,223,095 | A | 9/1980 | Esser et al. |
| 4,275,181 | A | 6/1981 | Hoh |
| 4,485,200 | A | 11/1984 | Perlinski et al. |
| 4,879,364 | A | 11/1989 | Stanislawczyk |
| 5,026,807 | A | 6/1991 | Ohira et al. |
| 5,140,072 | A | 8/1992 | Takeshita |
| 5,399,625 | A | 3/1995 | Glenn, Sr. |
| 5,407,993 | A | 4/1995 | Lyons et al. |
| 5,476,896 | A | 12/1995 | Pereira et al. |
| 5,567,771 | A | 10/1996 | Tsuji et al. |
| 5,681,891 | A | 10/1997 | Satoh et al. |
| 5,698,633 | A | 12/1997 | Matsumoto et al. |
| 5,767,214 | A | 6/1998 | Peresleni Rivet et al. |
| 5,767,215 | A | 6/1998 | Peresleni Rivet et al. |
| 5,881,387 | A | 3/1999 | Merovitz et al. |
| 5,910,533 | A | 6/1999 | Ghosal et al. |
| 6,000,061 | A | 12/1999 | Taneja et al. |
| 6,195,805 | B1 | 3/2001 | Bourne et al. |
| 6,306,514 | B1 | 10/2001 | Weikel et al. |
| 6,391,409 | B1 | 5/2002 | Yeh et al. |
| 6,403,722 | B1 | 6/2002 | Severe et al. |
| 6,566,435 | B1 | 5/2003 | Teoh et al. |
| 6,706,816 | B2 | 3/2004 | Williams et al. |
| 6,767,947 | B2 | 7/2004 | Musch et al. |
| 6,775,848 | B2 | 8/2004 | McGlothlin et al. |
| 6,828,387 | B2 | 12/2004 | Wang et al. |
| 6,844,385 | B1 | 1/2005 | Hagiwara et al. |
| 7,005,478 | B2 | 2/2006 | Williams et al. |
| 7,073,201 | B2 | 7/2006 | Sunada et al. |
| 7,665,150 | B2 | 2/2010 | Holley |
| 7,721,354 | B2 | 5/2010 | Yu et al. |
| 7,923,498 | B2 | 4/2011 | Foo |
| 8,028,348 | B2 | 10/2011 | Hull |
| 8,110,266 | B2 | 2/2012 | Chen et al. |
| 8,117,672 | B2 | 2/2012 | Lipinski |
| 8,118,969 | B2 | 2/2012 | Williams |
| 8,187,684 | B2 | 5/2012 | Teoh et al. |
| 8,250,673 | B2 | 8/2012 | Lipinski |
| 8,273,810 | B2 | 9/2012 | Wang et al. |
| 8,758,662 | B2 | 6/2014 | Lipinski |
| 8,980,391 | B2 | 3/2015 | Chen et al. |
| 9,080,025 | B2 | 7/2015 | Chen et al. |
| 9,085,663 | B2 | 7/2015 | Chen et al. |
| 9,179,717 | B2 | 11/2015 | Lipinski |
| 9,308,048 | B2 | 4/2016 | Venables et al. |
| 2002/0113143 | A1 | 8/2002 | Frost et al. |
| 2003/0050377 | A1* | 3/2003 | Hagiwara ............ B29C 41/003 524/418 |
| 2004/0010067 | A1 | 1/2004 | Ota et al. |
| 2005/0081278 | A1 | 4/2005 | Williams |
| 2005/0113527 | A1 | 5/2005 | Perrella |
| 2005/0171272 | A1 | 8/2005 | Ota et al. |
| 2006/0191056 | A1 | 8/2006 | Bottcher |
| 2006/0235158 | A1 | 10/2006 | Ota et al. |
| 2006/0257674 | A1* | 11/2006 | Lipinski ................ A61B 42/10 428/451 |
| 2007/0082152 | A1 | 4/2007 | Kodama |
| 2007/0149693 | A1 | 6/2007 | Aida et al. |
| 2007/0224395 | A1 | 9/2007 | Rowitsch et al. |
| 2008/0051498 | A1 | 2/2008 | Kodama |
| 2008/0125572 | A1 | 5/2008 | Ozoe |
| 2008/0299341 | A1 | 12/2008 | Renaud et al. |
| 2008/0306200 | A1 | 12/2008 | Chen et al. |
| 2009/0036608 | A1 | 2/2009 | Ozoe |
| 2009/0234064 | A1 | 9/2009 | Wang et al. |
| 2009/0326143 | A1 | 12/2009 | Laakso, Jr. et al. |
| 2012/0130008 | A1 | 5/2012 | Tamai et al. |
| 2014/0000006 | A1 | 1/2014 | Perera et al. |
| 2014/0011936 | A1 | 1/2014 | Hashimoto et al. |
| 2014/0137435 | A1 | 5/2014 | Yano |
| 2015/0128329 | A1 | 5/2015 | Amarasekera et al. |
| 2015/0135403 | A1* | 5/2015 | Mercado ............... C09D 109/02 2/164 |
| 2015/0143610 | A1 | 5/2015 | Pimentel de Oliveira et al. |
| 2015/0152209 | A1 | 6/2015 | Otsuka et al. |
| 2015/0218352 | A1 | 8/2015 | Enomoto et al. |
| 2015/0272241 | A1 | 10/2015 | Lucas et al. |
| 2015/0342274 | A1 | 12/2015 | Chen et al. |
| 2015/0376322 | A1 | 12/2015 | Nakamura et al. |
| 2016/0053095 | A1 | 2/2016 | Lipinski |
| 2017/0099889 | A1 | 4/2017 | Liou |
| 2017/0342243 | A1* | 11/2017 | Kato ..................... A41D 19/04 |
| 2018/0016409 | A1 | 1/2018 | Liou |

FOREIGN PATENT DOCUMENTS

| | | |
|---|---|---|
| CN | 103724742 A | 4/2014 |
| DE | 29617771 U1 | 2/1998 |
| DE | 102008040135 A1 | 1/2010 |
| EP | 0 451 998 A2 | 10/1991 |
| EP | 0 931 633 A2 | 7/1999 |
| EP | 1 541 630 A1 | 6/2005 |
| EP | 1 566 391 A2 | 8/2005 |
| EP | 1 607 420 B1 | 2/2011 |
| EP | 3 124 535 A1 | 2/2017 |

(56) References Cited

FOREIGN PATENT DOCUMENTS

| | | |
|---|---|---|
| GB | 806142 | 12/1958 |
| JP | H02227479 A | 9/1990 |
| JP | H0423877 A | 1/1992 |
| JP | H08-209093 A | 8/1996 |
| JP | H10-030034 A | 2/1998 |
| JP | 2001011201 A | 1/2001 |
| JP | 2004-359787 A | 12/2004 |
| JP | 2005154756 A | 6/2005 |
| JP | 2007106994 A | 4/2007 |
| JP | 2009-501833 A | 1/2009 |
| JP | 4342706 B2 | 10/2009 |
| JP | 2011-012196 A | 1/2011 |
| JP | 2011122141 A | 6/2011 |
| JP | 2012-180437 A | 9/2012 |
| JP | 5043423 B2 | 10/2012 |
| JP | 2012188552 A | 10/2012 |
| JP | 5428305 B2 | 2/2014 |
| JP | 5485119 B2 | 5/2014 |
| JP | 2014114342 A | 6/2014 |
| KR | 1020160046166 | 4/2016 |
| MY | 118694 A | 1/2005 |
| TW | 200819488 A | 5/2008 |
| WO | 1995/004766 A1 | 2/1995 |
| WO | 1995009197 A1 | 4/1995 |
| WO | 1999/024507 A1 | 5/1999 |
| WO | 1999024507 A1 | 5/1999 |
| WO | 2001090236 A1 | 11/2001 |
| WO | 2003/006513 A1 | 1/2003 |
| WO | 2004/044037 A1 | 5/2004 |
| WO | 2006027164 A1 | 3/2006 |
| WO | 2007/011309 A1 | 1/2007 |
| WO | 2007/026704 A1 | 3/2007 |
| WO | 2008/027757 A1 | 3/2008 |
| WO | 2008/067365 A2 | 6/2008 |
| WO | 2008135213 A1 | 11/2008 |
| WO | 2010/088713 A1 | 8/2010 |
| WO | 2012085587 A1 | 6/2012 |
| WO | 2015145867 A1 | 10/2015 |
| WO | 2015147010 A1 | 10/2015 |
| WO | 2016064173 A1 | 4/2016 |
| WO | 2017/116227 A1 | 7/2017 |

OTHER PUBLICATIONS

Joseph, Rani, "Practical Guide to Latex Technology", Smithers Rapra Technology, Ltd. (2013) (in English; 121 pages).

Klingender, Robert C., "Handbook of Specialty Elastomers", published by CRC Press, Taylor & Francis Group, (2008) (in English; 572 pages).

Office Action and Search Report dated Jan. 25, 2016 issued in counterpart Taiwanese patent application No. 103124491 (w/ English partial machine translation) (10 pages).

Radhakrishman et al., "Modification of Polychloropene by Graft Copolymerization and its Application as an Adhesive", The Journal of Adhesion, vol. 61, 1997, pp. 27-36; cited in the International Search Report (in English; 11 pages).

International Search Report and Written Opinion of the International Searching Authority dated Oct. 7, 2014 issued in counterpart application No. PCT/AU2014/000727 (in English; 10 pages).

International Preliminary Report on Patentability from the International Preliminary Examining Authority, dated Nov. 13, 2015, issued in counterpart application No. PCT/AU2014/000727; accompanied by annexes of amendments made under PCT Article 34 (in English; 35 pages).

Bhattacharya, A. et al., "Grafting: a versatile means to modify polymers: Techniques, factors and applications", Progress in Polymer Science, vol. 29, No. 8, 2004, pp. 767-814 (in English; 48 pages).

Bhattacharya, A. et al., "Polymer Grafting and Cross-Linking", published by John Wiley & Sons, Inc., 2009, title page (in English; 1 page).

Khan, A. A. and Brame, Jr., E. G., "Preparation and Characterization of Copolymers of Choroperene and Methyl Methacrylate", Journal of Polymer Science: Polymer Physics Edition, vol. 14, 1976, pp. 165-171 (cited in counterpart Australian patent application No. 2013902628; in English; 7 pages).

Iqbal, Tanveer et al., "Temperature Effects on Grafting Reaction to Produce Methyl Methacrylate Grafted Polychloroprene Adhesive", Journal of Pakistan Institute of Chemical Engineers, vol. 39, No. 1, 2011, pp. 75-80 (cited in counterpart Australian patent application No. 2013902628; in English; 9 pages).

Gorton, T., "Latex Product Manufacturing Technology", published in "Rubber Products Manufacturing Technology", (Ed) Bhowmick, A. K. et al., Chapter 28, Section 28.4.1., Steps 5-6, p. 829 (cited in co-pending International Patent Application No. PCT/AU2014/000726; in English; 5 pages).

* cited by examiner

ELASTOMERIC FILM-FORMING COMPOSITIONS AND ARTICLES MADE FROM THE ELASTOMERIC FILM

FIELD

The present invention relates to elastomeric film-forming compositions for use in manufacturing dipped articles, such as gloves, and methods for forming elastomeric films and gloves.

BACKGROUND OF THE INVENTION

Whenever a thin film glove is worn for barrier protection either by medical personnel or for industrial purposes the gloves will become uncomfortable to the wearer after a short time. This is due to the fatigue associated with the resistance of the glove caused by an intrinsic character known as "lesser elasticity", which is measured in terms of its modulus. A higher modulus glove material is less satisfactory for such gloves.

Gloves that are made from natural (polyisoprene) rubber have favorable feel and comfort properties. However, natural (polyisoprene) rubber is associated with potential allergen (which causes Type I allergy). In view of this allergenic property, natural (polyisoprene) rubber is generally not suitable for use in the manufacture of dipped articles, such as rubber gloves due to the adverse effect of natural (polyisoprene) rubber on the wearer.

The current trend is to use synthetic materials like nitrile rubber, polyisoprene, styrene butadiene rubber, butyl rubber and vinyl to produce dipped articles such as gloves. Over the past few years the volume of glove production using synthetic materials has increased substantially. However, nitrile rubber, styrene butadiene rubber, butyl rubber and vinyl are not able to provide the favorable feel and comfort of natural (polyisoprene) rubber. While synthetic polyisoprene can provide a favorable feel and comfort that is comparable to that of natural (polyisoprene) rubber, synthetic polyisoprene is very expensive and is not suitable for use in the manufacture of some articles such as thin film gloves, which are used in high volumes and discarded.

Polychloroprene is a synthetic material that has been found to exhibit a similar texture, feel and softness as natural polyisoprene. Polychloroprene differs from natural polyisoprene in that the methyl group at the 2-position of the isoprene monomer is replaced with chlorine. However, conventional polychloroprene is very expensive and processing of polychloroprene requires a high energy input. In addition to these problems, a higher film thickness and high level of curing chemicals (almost 3-4 times that of natural polyisoprene) is required. For at least these reasons, conventional polychloroprene is not preferred for use in the manufacture of some articles, such as rubber gloves and particularly gloves that are discarded after a single use.

Elastomeric compositions such as those described above have the potential for application in articles other than gloves. For example, dipped articles may be configured for use in medical applications such as surgical gloves, examination gloves, catheters, tubing, protective covering, balloons for catheters, condoms and like, or for use in non-medical applications, such as industrial gloves, laboratory gloves, household gloves, gardening gloves, electrical gloves, irradiation gloves, finger cots, weather balloons, clean room gloves for electronic industries, gloves for food contact and food processing and biotechnical applications and the like. New developments in this field may identify further applications for these types of dipped articles that have not yet been identified.

There is a therefore a need for alternative or improved dipped articles, including compositions for forming these articles and methods of manufacturing the articles.

SUMMARY

The present inventors have found that the selection of a carboxylic acid- or ester-grafted polychlorobutadiene as a component of an elastomeric film-forming composition can be used to prepare dipped articles, such as gloves, which have improved properties. The composition of the invention can be used to prepare very thin layers of elastomeric film using a minimal amount of polymeric material while still maintaining suitable properties such as elasticity, strength, durability and the absence of defects like pin holes or weak spots.

In one embodiment, there is provided an elastomeric film-forming composition comprising: (a) a carboxylic acid- or ester-grafted polychlorobutadiene, and (b) one or more cross-linking agents. The elastomeric film-forming composition of the present invention is not a simple physical blend of polychloroprene with other synthetic material. Instead, the elastomeric film-forming composition contains a polymer that is a carboxylic acid- or ester-grafted polychlorobutadiene. In other words, the elastomeric film-forming composition of the present invention comprises a single polymer consisting of chlorobutadiene units to which one or more carboxylic acid residues or esters thereof are grafted. In these polymers the carboxylic acid residues are covalently attached to the chlorobutadiene units as substituents on the polychlorobutadiene. In some embodiments, there are no carboxylic acid groups in the main chain of the polymer. In some cases, minor changes to the structure of a polymer may have a significant effect on the properties of elastomeric films or dipped articles produced using the polymer. In one embodiment, the elastomeric film-forming composition of the invention can be used to form thinner layers of elastomeric film. In another embodiment, the elastomeric film-forming composition of the invention can be used to prepare dipped articles, such as gloves, which may have improved properties such as improved feel, improved softness or increased elasticity.

Using a carboxylic acid- or ester-grafted polychlorobutadiene provides advantages when compared to the use of a blend of, for example, a polychloroprene and a polymer of carboxylic acid containing monomers. For example, dipped articles prepared from the elastomeric film-forming composition of the invention may possess improved physical properties. In some embodiments, the dipped articles prepared from the elastomeric film-forming composition of the invention have a higher tensile value at break, a lower modulus at 300% and/or a lower modulus at 500% and/or a higher elongation to break when compared to elastomeric film compositions containing blends of polychloroprene and a polymer of carboxylic acid containing monomers. In some embodiments, the dipped articles prepared from the elastomeric film-forming composition of the invention have a tensile strength of greater than or equal to about 2000 psi, a modulus at 300% of about 100 to 2000 psi, a stress at 500% of about 200 to 3000 psi, and/or an elongation to break of about 400 to 1500%. Preferably, the dipped articles prepared from the elastomeric film-forming composition of the invention have a tensile value at break of greater than 2100 psi, a modulus at 300% of less than 660 psi and/or a modulus at 500% of less than about 2400 psi and more preferably less than about 1015 psi and/or an elongation to break of greater than 520%, and preferably greater than 650%. In some embodiments, the improvements may be even better when using the combination of one or more cross-linking agents, such as a combination of an ionic cross-linking agent (for example a metal oxide or a metal hydroxde) and a covalent cross-linking agent (for example sulphur or a sulphur-containing vulcanising agent). In other embodiments, the improvements may be even better when using a carboxylic acid- or ester-grafted polychlorobutadiene having a selected degree of carboxylation.

In another embodiment, there is provided an elastomeric film comprising at least one layer of a cured composition comprising a carboxylic acid- or ester-grafted polychlorobutadiene, and one or more cross-linking agents. The elastomeric film may be made from an elastomeric film-forming composition according to any of the embodiments of the composition described herein. The elastomeric film may be in the form of a dipped article, where a former in the shape of an article is dipped into the elastomeric film-forming composition and the composition is cured on the former.

In yet another embodiment, there is provided a dipped article made from an elastomeric film comprising at least one layer of a cured composition comprising a carboxylic acid or ester-grafted polychlorobutadiene, and one or more cross-linking agents. The dipped article may be made from an elastomeric film-forming composition according to any of the embodiments of the composition described herein.

Dipped articles, such as gloves made using the composition of the present invention have been found to possess favourable characteristics such as favourable feel and comfort, improved softness and can be made from very thin layers of elastomeric film without increasing the presence of defects such as pin holes, weak spots or other defects. Elastomeric film-forming compositions that can be used to form very thin layers of elastomeric film without compromising the elasticity, strength, durability or other characteristics such as feel, comfort, softness or the absence of defects, allows the film to be suitable for use in specific applications such as, for example, in medical examination gloves and surgical gloves, where it is important that the film does not prevent the wearer from having good tactile perception.

In yet another embodiment, there is provided a glove comprising at least one layer of elastomeric film comprising a carboxylic acid or ester-grafted polychlorobutadiene, and one or more cross-linking agents. The glove may be made from an elastomeric film-forming composition according to any of the embodiments of the composition described herein.

The present inventors have identified that a polymer comprising a carboxylic acid- or ester-grafted polychlorobutadiene can be used to prepare dipped articles having improved properties. The dipped articles prepared from the elastomeric film-forming composition of the invention retain the favourable feel and comfort that is closer to natural rubber film yet is free of proteins and other potential allergens (causing Type I allergy) associated with natural rubber. Where the dipped article is a glove, retaining the properties of natural rubber gloves also means that the products are easily donnable without any visible powder anti tack material. In addition, the dipped articles prepared from the elastomeric film-forming composition of the invention also possess improved physical properties. In some embodiments, the dipped articles prepared from the elastomeric film-forming composition of the invention have a higher tensile strength, a lower modulus at 300%, a lower modulus at 500% and/or a higher elongation to break when compared to other elastomeric films used to form dipped articles or gloves. In some embodiments, the dipped articles prepared from the elastomeric film-forming composition of the invention have a tensile strength of greater than or equal to about 2000 psi, a modulus at 300% of about 100 to 2000 psi, a stress at 500% of about 200 to 3000 psi, and/or an elongation to break of about 400 to 1500%. For example, the elastomeric film prepared from the composition of the present invention has a tensile strength of at least about 2100 psi, a modulus at 300% of less than 660 psi, a stress at 500% of less than about 2400 psi and more preferably less than about 1015 psi, and/or an elongation to break of greater than 520% and preferably greater than about 650%. This improvement may be even better when using selected cross-linking agents or when using an elastomeric film-forming composition that contains a carboxylic acid- or ester-grafted polychlorobutadiene in which the carboxylic acid group or ester group is present in a selected amount.

In some embodiments, the combination of an ionic cross-linking agent (for example a metal oxide or a metal hydroxide) and a covalent cross-linking agent (for example sulphur or a sulphur-containing vulcanising agent) as the cross-linking agents with a carboxylic acid- or ester-grafted polychlorobutadiene provides an elastomeric film having improved properties. In other embodiments, the cross-linking agent may be selected from, but not restricted to accelerators (including the carbamates such as thiocarbamates (e.g. zinc dibutyl dithiocarbamate (ZDBC), zinc diethyl dithiocarbamate (ZDEC)), thiurams (e.g. tetraethylthiuram disulfide (TETD), tetramethylthiuram disulphide (TMTD)), thiourea (Ethyl thiourea (ETU) and diphenylthiourea (DPTU)), thiazoles (e.g. mercapto benzothiazoles (MBT), mercapto benzothiozole disulphide (MBTS), zinc 2-mercaptobenzothiazole (ZMBT)), guanidines (eg. Diphenylguanidine (DPG)) and aldehyde/amine-based accelerators (e.g. hexamethylenetetramine)); ionic cross-linking agents including organic and inorganic metal oxides, organic and inorganic metal hydroxides and organic and inorganic peroxides (including the multivalent metal oxide cross-linking agents, such as lead oxide, magnesium oxide, barium oxide, zinc oxide, manganese oxide, copper oxide, nickel oxide, aluminium oxide, barium hydroxide, manganese hydroxide, copper hydroxide, nickel hydroxide, aluminium hydroxide, 1,1-di(t-butylperoxy)-3,3,5-trimethylcyclohexane and combinations thereof); cross-linking monomers; reactive oligomers; polyisocyanate oligomers; functional, cross-linkable polymers; derivatives of ethylene glycol di(meth) acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrylate (TEDMA)); derivatives of methylenebisacrylamide (such as N,N.-methylenebisacrylamide, N,N.-methylenebisacrylamide, N,N.-(1,2 dihydroxyethylene)bisacrylamide); formaldehyde-free crosslinking agents (such as N-(1-Hydroxy-2,2-dimethoxyethyl)acrylamide); divinylbenzene; divinylether; diallyl phthalate; divinylsulfone and the like. In one embodiment, the cross-linking agent comprises a metal oxide or a metal hydroxide and sulphur or a sulphur-containing vulcanising agent.

In some embodiments, the elastomeric film-forming composition of the invention contains a carboxylic acid- or ester-grafted polychlorobutadiene in which the carboxylic acid group or ester group is present in an amount of from 0.01% to 8% by weight of chlorobutadiene units present in the polymer. Using a carboxylic acid- or ester-grafted polychlorobutadiene having this amount of carboxylic acid or ester groups provides an elastomeric film having improved properties.

Polychloroprene differs from natural polyisoprene in that the methyl group at the 2-position of the isoprene monomer is replaced with chlorine. Polychloroprene exhibits a similar texture, feel and softness as natural polyisoprene, but as described above in relation to natural polyisoprene, polychloroprene is very expensive and is not preferred for use in the manufacture of articles such as rubber gloves, and particularly gloves that are discarded after a single use. In addition, the processing of polychloroprene requires a high energy input, a higher film thickness and high level of curing chemicals (almost 3-4 times that of natural polyisoprene). For at least these reasons, polychloroprene is not preferred for use in the manufacture of some articles.

Using a carboxylic acid- or ester-grafted polychlorobutadiene provides advantages when compared to the use of polychloroprene alone. As one example, if a composition of polychloroprene alone is used to prepare gloves that satisfy industry requirements, the gloves generally need to be thicker and require a greater amount of polymeric material to be used per glove. One disadvantage of thicker gloves can be seen in surgical gloves and medical examination gloves, where thicker gloves reduce sensitivity for the wearer. Accordingly, a balance must be struck in order to produce an elastomeric film having an appropriate thickness, using a minimal amount of polymeric material and in satisfying industry requirements for the specific application that the resulting article is to be used. The present inventors have found that gloves or other articles prepared from the elastomeric film-forming composition of the invention possess excellent characteristics or properties such as favourable feel and comfort, and improved softness. Gloves or other articles prepared from the elastomeric film-forming composition of the invention can be made from very thin layers of elastomeric film and using a minimal amount of polymeric material while still maintaining industry requirements for the specific applications such as elasticity, strength, durability and the absence of defects like pin holes or weak spots. The use of less polymeric material also means that the product can be produced at a lower cost.

The present inventors have also identified that the elastomeric film-forming composition allows for simple processing with considerable savings in the required energy input, in the material of construction and in the chemical consumption for production of articles with the composition of the invention. Articles produced using this composition can be produced at lower cost and can be manufactured with fewer processing hurdles, without compromising the benefits provided using a polychloroprene (for example, the favorable feel and comfort). Therefore, the resulting articles may provide the favorable properties of natural rubber latex, such as comfort for the wearer where the article is for example a glove, and avoids the problem of Type I allergy associated with natural rubber latex. In some embodiments, the amount of chemicals and materials used in the preparation of dipped articles may be reduced when the elastomeric film-forming composition of the invention is used. In some embodiments, the amount of cross-linking agents such as zinc oxide that is used in the elastomeric film-forming composition of the invention may be reduced by up to 50% when compared with other compositions. The reduction in the amount of chemicals and materials used may produce dipped articles having improved properties and may also minimise manufacturing costs. In some embodiments, a minimal amount of polymeric material and/or a reduced amount of chemicals and materials may be used to make elastomeric films while maintaining the necessary industry requirements for certain applications such as elasticity, strength, durability and the absence of defects like pin holes or weak spots. The use of less polymeric material also means that the product can be produced at a lower cost.

In a further embodiment, there is provided a method of manufacturing an elastomeric film comprising the steps of: (i) dipping a former into a composition as described above to produce a layer of elastomeric film-forming composition on the former, and (ii) drying and curing the elastomeric film-forming composition.

In one embodiment, the method will further comprise, prior to step (i), the steps of: (a) dipping the former into a coagulant, followed by (b) drying or partially drying the coagulant-dipped former.

In another embodiment, the method will further comprise, following step (ii), the steps of:
 (iii) dipping the former into a composition as described above to produce a further layer of elastomeric film-forming composition on the former,
 (iv) optionally repeating the drying step (ii) and the further dipping step (iii), and
 (v) drying and curing the layered elastomeric film.

In some embodiments, the drying step and the dipping step are repeated to produce a film having from 2 to 15 layers. For example, a method for producing a film having two layers will require that the drying step and the further dipping step are repeated at least once.

In a still further embodiment, there is provided a multiple-coating method of manufacturing a layered elastomeric film comprising the steps of:
 (i) dipping a former into a composition as described above to produce a layer of elastomeric film-forming composition on the former,
 (ii) drying or partially drying the elastomeric film-forming composition,
 (iii) dipping the former into a composition as described above to produce a further layer of elastomeric film-forming composition on the former,
 (iv) optionally repeating the drying step (ii) and the further dipping step (iii), and
 (v) drying and curing the layered elastomeric film.

In a still further embodiment, there is provided an elastomeric film produced by the method as described above. The elastomeric film produced by the method as described above may involve the elastomeric film-forming composition according to any of the embodiments of the composition described herein.

In a still further embodiment, there is provided the use of an elastomeric film-forming composition comprising a carboxylic acid- or ester-grafted polychlorobutadiene, and one or more cross-linking agents, in the manufacture of a glove. The use may involve the elastomeric film-forming composition according to any of the embodiments of the composition described herein.

Additional details concerning the dipped articles, their properties and their manufacture are described in further detail below.

BRIEF DESCRIPTION OF THE DRAWINGS

Preferred embodiments of the present invention will now be further described and illustrated, by way of example only, with reference to the accompanying drawing in which.

DETAILED DESCRIPTION

Figure 1:
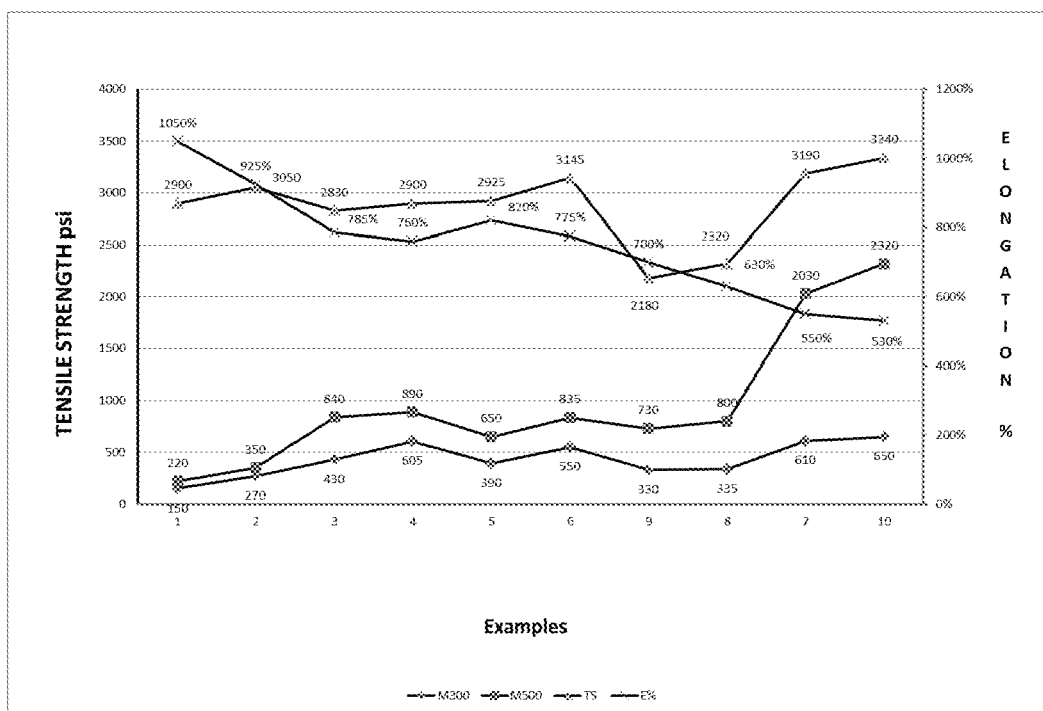
FIG. 1 is a graph showing the experimental results obtained for the elastomeric films obtained from the compositions of Examples 1 to 10. The left hand axis shows the values obtained in psi for the tensile strength, the modulus at 300% and the modulus at 500%, while the right hand axis shows the values obtained in % for the elongation to break. Examples 1 and 2 used a composition containing a carboxylic acid-grafted polychloroprene having a carboxylation level of 1.5 and 2.5%, respectively, without blending with a second elastomer. Examples 3, 4, 5 and 6 used a composition containing nitrile butadiene rubber as a second elastomer in an amount of 15 phr. Examples 3 and 4 used compositions containing the same amount of cross-linking agents (5 phr ZnO, 1 phr sulphur and 1 phr ZDBC), while Examples 5 and 6 used compositions containing a lower amount of cross-linking agents (2.5 phr ZnO, 0.5 phr sulphur and 0.5 phr ZDBC). Examples 3 and 5 used a composition containing a carboxylic acid-grafted polychloroprene having a carboxylation level of 1.5%, while Examples 4 and 6 used a composition containing a carboxylic acid-grafted polychloroprene having a carboxylation level of 2.5%. Examples 9, 8, 7 and 10 used a composition containing nitrile butadiene rubber as a second elastomer in an amount of 30%, 45%, 75% and 95% by weight of the polymer component of the composition on a dry basis. Examples 9, 8, 7 and 10 used a composition containing a carboxylic acid-grafted polychloroprene having a carboxylation level of 0.01%. The amount of ZnO used in the composition of Examples 9, 8, 7 and 10 was 4 phr, 3 phr, 2 phr and 1.2 phr, respectively. The amount of sulphur used in the composition of Examples 9, 8, 7 and 10 was 1.5 phr. The amount of ZDBC used in the composition of Examples 9, 8, 7 and 10 was 1.5 phr, 1.25 phr, 1.0 phr and 0.8 phr, respectively.

The elastomeric film-forming composition, dipped articles, gloves, methods of manufacture and uses thereof, according to particular embodiments of the invention are described below.

The present invention relates, in particular, to compositions containing a carboxylic acid- or ester-grafted polychlorobutadiene, and to dipped articles, such as gloves or other products, which are made from the composition. It will be appreciated that the composition of the invention could be modified, such as by the addition of additives or by altering the relative amounts of other components, to suit the purpose of the dipped article or glove made from the composition.

Elastomeric Film-Forming Composition

The elastomeric film-forming composition comprises a dispersion or emulsion of a polymer containing chlorobutadiene units and one or more carboxylic acid residues or esters thereof in a liquid. The composition generally comprises the polymer as well as cross-linking agents in the liquid medium.

The liquid medium is typically water, although other solvents such as alcohols (including aliphatic alcohols and aromatic alcohols) or aromatic solvents may be used. Examples of suitable solvents include water, methanol, ethanol, n-propanol, isopropanol, n-butanol, butanediol, diethanolamine, butoxyethanol, ethylene glycol, glycerol, methyldiethanolamine, propanediol, pentanediol, propylene glycol, triethylene glycol, furfural alcohol, benzyl alcohol, benzene, toluene, xylene, pyridine, tetrahydrofuran, benzonitrile, chlorobenzene and 1,2-dichlorobenzene. Preferably, the solvent used is water. When water is used, the polymer is in colloidal form and processing and handling are simplified.

A solvent, or preferably water, is added as a diluent in an amount to reach the required total solids content of the total composition, or the required total solids content of the polymer component of the elastomeric film-forming composition. In one embodiment, the solvent comprises from 40 to 95% by weight of the total composition. In another embodiment, the composition contains water in an amount of from 40 to 95% by weight of the total composition. Other optional components, as described in further detail below, may also be present in the composition.

The total solids content of the polymer component of the elastomeric film-forming composition is from 5% to 60% by weight of the composition. The polymer component of the elastomeric film-forming composition includes the amount of the carboxylic acid- or ester-grafted polychlorobutadiene and, where present, the amount of the second elastomer. The percentage of total solids content (TSC %) can vary within this range. Preferably, the total solids content of the polymer component of the elastomeric film-forming composition is about 5 to 55%, 10 to 60%, 10 to 55%, 15% to 60%, 15% to 55%, 20% to 60%, 20% to 55%, 5% to 50%, 10% to 50%, 20% to 50%, 30% to 60%, 30% to 55%, 30% to 50%, 35% to 60%, 35% to 50%, 40% to 60%, 40% to 55%, 40% to 50%, 45% to 60%, 45% to 55% or 45% to 50%.

The polymer component plus the other components of the elastomeric film-forming composition are diluted with a liquid medium (such as water) to reach the desired concentration. The total solids content of the elastomeric film-forming composition is from 5% to 60% by weight of the composition. The percentage of total solids content (TSC %) can vary within this range. Preferably, the total solids content of the elastomeric film-forming composition is about 5 to 55%, 10 to 60%, 10 to 55%, 15% to 60%, 15% to 55%, 20% to 60%, 20% to 55%, 5 to 50%, 10% to 50%, 20% to 50%, 30% to 60%, 30% to 55%, 30% to 50%, 35% to 60%, 35% to 50%, 40% to 60%, 40% to 55%, 40% to 50%, 45% to 60%, 45% to 55% or 45% to 50%.

Generally, for forming a thin or disposable type of glove such as a surgical glove or medical examination type glove, the total solids content will be towards the lower end of this range. For example, the total solids content may be within one of the following ranges: 5 to 50%, 10 to 50%, 5 to 40%, 10 to 40%, 5 to 35%, 10 to 35%, 5% to 30%, 10 to 30%, 5% to 25%, 10 to 25%, 5% to 20%, 10 to 20%, 15% to 50%, 15% to 40%, 15% to 35%, 15% to 30%, 15% to 25%, 15% to 20%, 20% to 50%, 20% to 40%, 20% to 35%, 20% to 30%, 20% to 25%, 25% to 35%, 35% to 40% or 35%-50%. For forming thicker gloves such as household gloves or industrial gloves, the total solids content will tend to be higher or the glove will be produced from many more layers. Thus, for thicker gloves, the total solids content will tend to be within one of the following ranges: 5% to 60%, 10 to 60%, 15 to 60%, 20 to 60%, 25 to 60%, 30% to 60%, 35% to 60%, 40-60%, 5 to 55%, 10% to 55%, 15 to 55%, 20 to 55%, 25 to 55%, 30% to 55%, 35% to 55%, 40% to 55%, 5 to 50%, 10% to 50%, 15 to 50%, 20 to 50%, 25 to 50%, 30% to 50%, 35% to 50%, 40% to 50%, 45-55%, 50-60%, or 40-50%.

The elastomeric film-forming composition of the invention can be used to form a self-supported or unsupported film. A self-supported or unsupported film is a film that exists without other structural components or layers that the film is adhered to or attached to.

In the art of the present invention, it is common to refer to the amount of the polymer as being 100 phr (per hundred parts "rubber"), and for the relative amounts of the remaining components of the elastomeric film-forming composition to be calculated as a number of parts compared to the 100 phr of the polymer, by weight. Thus, for an amount of cross-linking agent that is 1/100th that of the polymer in the composition by weight, the amount of cross-linking agent is referred to as 1.0 phr.

It is also common in the art to use the expression "latex" or "rubber" to refer to any polymer in a general sense. Accordingly, particularly in the examples which follow, it should be understood that these terms have been used as short-hand to refer to the polymer of the dipping composition.

Polymer

The polymer that is used in the elastomeric film-forming composition of the present invention comprises a single polymer consisting of chlorobutadiene units, to which one or more carboxylic acid residues or esters thereof are grafted. In these polymers the carboxylic acid residues are covalently attached to the chlorobutadiene units which form the backbone of the polymer.

The polymer may be referred to as a "carboxylate or ester substituted polychlorobutadiene" or a "carboxylate or ester grafted polychlorobutadiene".

The polymer backbone may be a homopolymer containing one type of chlorobutadiene monomer, or a copolymer containing two or more different chlorobutadiene monomers. Similarly, the carboxylic acid residues or esters thereof that are grafted to the polymer backbone may consist of one type of carboxylic acid residues or esters thereof or more than one type of carboxylic acid residues or esters thereof.

The polychlorobutadiene backbone comprises chlorobutadiene units. In some embodiments, there are no carboxylic acid groups or esters thereof in the main chain of the polymer. The carboxylic acid residues are covalently attached to the chlorobutadiene units as substituents on the polychlorobutadiene. The polymer may be referred to as a "carboxylic acid- or ester-substituted polymer" or a "carboxylic acid- or ester-grafted polymer".

The stability of polychloroprene in general is poor compared to other latexes due to decomposition by autocatalytic dehydrochlorination. Therefore, polychloroprene is generally prepared at high pH to avoid such decomposition. In the present case, the carboxylic acid- or ester-grafted polychlorobutadiene may be prepared at a pH in the range of from about 8.5 to about 13.5. Preferably, the carboxylic acid- or ester-grafted polychlorobutadiene has a pH in the range of from about 8.5 to 11, 9.0-11.5, 9.5-12, 10-12.5, 11-13, 11.5-13.5. It will be appreciated that the pH could be modified, such as by the addition of acid or base to suit the purpose of the composition.

The shelf life of the carboxylic acid- or ester-grafted polychlorobutadiene used in the elastomeric film-forming composition of the present invention may be affected by the presence of carboxyl groups. In some cases, the polymer and/or the elastomeric composition may be stored at lower temperature and the pH monitored and adjusted (for example, by addition of alkaline solutions preferably potassium hydroxide and/or ammonium hydroxide), where necessary.

Carboxylate- or Ester-Grafted Polychlorobutadiene

The carboxylate- or ester-grafted polymer could be prepared by grafting one or more carboxylic acid residues or esters thereof onto a polymer containing chloroprene units. The grafting step may be performed by the supplier and the polymer provided to the manufacturer as the carboxylic acid- or ester-grafted polymer for use in the preparation of the elastomeric film-forming composition and ultimately the manufacture of elastomeric films or dipped articles such as gloves. The grafting step may also be performed by the manufacturer as a first step in the preparation of the elastomeric film-forming composition.

In the case where the grafting step is performed by the manufacturer, the flexibility in the grafted polymer produced may allow improved processability, improved properties for the film or dipped articles produced from the composition and may result in a saving in the amount of material used in making the film.

It is often the case that commercially available polymer formulations can vary and there may be differences between the polymers provided by different suppliers. Therefore, where the manufacturer performs the grafting step in situ, the grafted polymer can be produced with improved consistency, and the manufacturer can control the type of grafted polymer produced or make certain adjustments to the grafting process to make a grafted polymer that is most suitable for the intended application of the elastomeric films or dipped articles that are ultimately produced.

As one example, the processes may be customised to produce a grafted polymer having a particular amount of carboxylic acid or ester grafted to the polymer backbone. Carboxylic acid- or ester-grafted polychlorobutadiene having a higher amount of carboxylic acid or ester in the polymer may be preferred for some applications, while a carboxylic acid- or ester-grafted polychlorobutadiene having a lower amount of carboxylic acid or ester in the polymer may be preferred for other applications. Conducting the grafting process in situ allows the manufacturer to control parameters such as the amount of carboxylic acid or ester grafted to the polymer backbone and to tailor the elastomeric film-forming composition for its end use.

The grafting step is performed using standard methods, and it will be appreciated that any suitable grafting technique could be used to make the polymer from polychloroprene and suitable carboxylic acids or esters thereof. The grafting step may be performed by one of the various methods described in "Polymer Grafting and Cross-linking" Edited by Dr. Amit Bhattacharya, Dr. James W. Rawlins, and Dr. Paramita Ray, John Wiley & Sons, Inc., 2009, and in "Grafting: a versatile means to modify polymers: Techniques, factors and applications" Bhattacharyaa, A. and Misrab, B. N., *Progress in Polymer Science,* 2004, Volume 29, Issue 8, pages 767-814, the contents of which are incorporated herein by reference.

Grafting is a method of modifying a polymer or a copolymer of chlorobutadiene by covalently bonding carboxylic acid or ester groups to the polymer chain. In particular, grafting is used to prepare a carboxylic acid- or ester-grafted polychlorobutadiene.

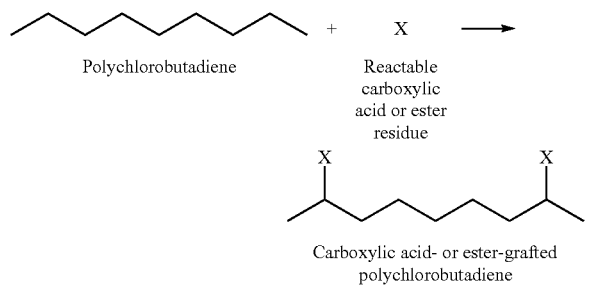

The grafting may be achieved by chemical means (for example by free radical or ionic reaction), using radiation, photochemical or plasma-induced techniques, or by enzymatic grafting.

As one example, the grafted polymer may be formed by preparing a solution containing a polymer of chloroprene units and adding a reactable carboxylic acid or ester residue. The polymer of chloroprene units and the reactable carboxylic acid or ester residue may then be subjected to free radical or ionic reaction, exposed to radiation, a photochemical stimulus, plasma-induced techniques or an enzyme in order for the reactable carboxylic acid or ester residues to be covalently attached to the polymer of chloroprene units.

In some embodiments, grafting is by chemical means and an initiator produces free radicals, which are transferred to the polymer and subsequently react with the reactable carboxylic acid or ester residue to form the carboxylic acid- or ester-grafted polymer. In other embodiments, irradiation may be used to form free radicals on the polymer, which then react with the reactable carboxylic acid or ester residue to form the carboxylic acid- or ester-grafted polymer. In general, the generation of free radicals can occur by indirect or direct methods. One example of the production of free radicals by an indirect method is the production of free radicals through redox reaction, such as with persulfates. In some embodiments, a redox catalyst system is used.

In some embodiments, a carboxylic acid- or ester-grafted polychlorobutadiene is prepared by combining a polychlorobutadiene polymer with a reactable carboxylic acid or ester residue in the presence of a cross-linking agent or chain-transfer agent. The cross-linking agent or chain transfer agent may, for example be diisopropyl xanthogen disulphide or an emulsifier stabilizer such as polyvinyl alcohol (PVA). The polychlorobutadiene polymer, the reactable carboxylic acid or ester residue and the cross-linking agent or chain-transfer agent may be combined in solution and may be emulsified to form an oil-in-water emulsion. Catalysts may be added as required to initiate and maintain the grafting process. Examples of suitable catalysts include sodium sulphite and potassium persulphate.

Grafting is typically carried out until the reactable carboxylic acid or ester residue is largely or completely grafted onto the polymer. For example, complete conversion may be achieved when greater than 90% and preferably about 98% of the reactable carboxylic acid or ester residue has been grafted onto the polychlorobutadiene. The extent of grafting may be verified by determining the amount of unreacted carboxylic acid or ester using analytical methods, and subtracting this amount from the amount of carboxylic acid or ester added.

It will be appreciated that any other suitable grafting technique could be used to make the carboxylic acid- or ester-grafted polychlorobutadiene. Furthermore, the grafting technique used could be modified, such as by the addition of catalysts, by using different cross-linking agents or chain-transfer agents or by altering the relative amount of the components.

In some cases, it is important to control the pH during grafting, as the carboxylic acid group lowers the pH and may destabilize the chloroprene polymer. Typically, the grafting step is performed with slow addition of the carboxylic acid residues or esters thereof.

Grafting of polychloroprene latex by combining the carboxylic acid group or derivative thereof (esters-acrylates) at the glove manufacturer end is possible with due care. It may be necessary to use suitable pH modifiers, and/or emulsifying agents to perform the grafting step. Preferably, the polymer containing chloroprene units is grafted with esters of carboxylic acid residues and optionally subsequently converting the esters to carboxylic acid residues. In some cases the carboxylic acid residue may destabilize the polymer, or may be hazardous. It may also be necessary to strip off the unreacted carboxylic acid residues.

Chlorobutadiene Units

Any chlorinated butadiene units may be used to form the carboxylic acid- or ester grafted polychlorobutadiene of the present invention. Examples of suitable chlorobutadiene units include 2-chloro-1,3-butadiene, 2,3-dichloro-1,3-butadiene and combinations thereof.

In one embodiment, a combination of 2-chloro-1,3 butadiene and 2,3-dichloro-1,3-butadiene are present in the polymer backbone, which may be subsequently grafted with the carboxylic acid or ester thereof. In another embodiment, 2-chloro-1,3 butadiene or 2,3-dichloro-1,3-butadiene are used to form a homopolymer, which may be subsequently grafted with the carboxylic acid or ester thereof.

The number and type of chlorobutadiene units present in the polymer that is used in the elastomeric film-forming composition may vary, and will depend on the purpose for which the composition will be used. The number of chlorobutadiene units, and the extent of chlorination of those chlorobutadiene units can be expressed as a percentage by weight of the chlorobutadiene units present in the polymer.

In order to produce a polymer having a specific level of chlorination, the polychlorobutadiene can be prepared by adjusting the relative amounts of chlorobutadiene and dichlorobutadiene used to form the polychlorobutadiene.

In one embodiment, the polymer comprises from about 10 to about 60% chlorine by weight of the chlorobutadiene units present in the polymer. Preferably, the polymer comprises from about 10% to about 58%, about 25% to about 60%, about 25% to about 58%, about 30% to about 60%, about 30% to about 58%, about 30% to about 45% or about 35% to about 45% chlorine by weight of the chlorobutadiene units present in the polymer. More preferably, the polymer comprises about 40% chlorine by weight of the total polymer.

Where the chlorine content is at the lower end of this range, the resulting dipped article will be softer, more stable and of nominal strength. Where the chlorine content is at the higher end of this range, the resulting dipped article will be tougher. It is believed that the higher chlorine content increases the molecular weight and increased bonding reactivity with ZnO.

Where a lower chlorine content is used, the elastomeric film-forming composition may be suitable for use in applications such as surgical gloves, where a softer or more elastic film is able to provide the wearer with good tactile perception. For example, the chlorine content suitable for production of thinner, softer and more elastic films may be in the range of about 10 to 50%, such as about 10 to 45%, about 25% to 45%, about 10 to 40%, about 25% to 40%, about 30 to 45%, about 30 to 40%, about 10 to 35%, about 25% to 35%, about 20% to 30% or about 10 to 30%.

Where a higher chlorine content is used, the elastomeric film-forming composition may be suitable for use in applications such as household gloves, industrial or heavy duty gloves, where a more rigid, less elastic film is required. For example, the chlorine content suitable for production of more rigid, less elastic films may be in the range of about 30 to 60%, such as about 30 to 58%, about 35 to 60%, about 35 to 58%, about 40 to 60%, about 40 to 58%, about 40 to 55%, about 45 to 60%, about 45 to 58%, about 40 to 50%, about 50 to 60% or about 50 to 58%.

Carboxylic Acid Residues

Any carboxylic acid or ester residues may be used in the elastomeric film-forming composition of the present invention. As one example, the carboxylic acid or ester thereof may simply be a carboxylic acid substituent, —C(O)—OH, or an ester thereof, —C(O)—OR, wherein R is an alkyl group. In some embodiments, the alkyl group has from 1 to 10 carbon atoms or from 1 to 4 carbon atoms. As another example, the carboxylic acid or ester may be a carboxylic acid or ester-containing monomer.

Suitable carboxylic acid or ester-containing monomers include ethylenically unsaturated carboxylic acid or esters thereof. The carboxylic acid and/or derivative could be of any type, including saturated or unsaturated, mono, di, tri or multi carboxylic acid, or may be aliphatic or aromatic in nature. Examples of suitable carboxylic acids include methacrylic acid, acrylic acid or terepthalic acid. Examples of suitable carboxylic acid derived esters are vinyl acetate, methyl acrylate, methacrylate ester, ethylenediol dimethacrylate and/or other related acrylate monomers.

In one embodiment, the carboxylic acid or ester has the formula:

$CR^1H=CR^2-C(O)-OR^3$ or $CR^1H=CR^2-O-C(O)-R^3$ wherein
$R^1$ is hydrogen, an alkyl radical containing 1 to 4 carbon atoms, —C(O)—OR$^4$ or —R$^5$—C(O)—OH, wherein $R^4$ is hydrogen or an alkyl radical containing 1 to 4 carbon atoms and $R^5$ is an alkyl radical containing 1 to 4 carbon atoms;
$R^2$ is hydrogen, an alkyl radical containing 1 to 4 carbon atoms, or a carboxymethyl radical;
$R^3$ is hydrogen, an alkyl radical containing 1 to 4 carbon atoms, or
—$R^6$O—C(O)—CR$^7$=CR$^8$, wherein $R^6$ is an alkyl radical containing 1 to 4 carbon atoms, and $R^7$ and $R^8$ are each independently hydrogen or an alkyl radical containing 1 to 4 carbon atoms; and
cis or trans isomers thereof.

Examples of suitable carboxylic acids or esters include acrylic acid, methacrylic acid, crotonic acid, fumaric acid, maleic acid, citraconic acid, glutaconic acid, vinyl acetate, methyl acrylate, methacrylate ester, ethylenediol dimethacrylate, butanediol dimethacrylate (for example, the commercially available 1,3, BDDMA by BASF could be used), methyl methacrylate (for example, the commercially available MMA by The DOW Chemical Company or Rohm&Haas), butyl methacrylate (BMA) and glacial methacrylic acid (GMAA), other related acrylate monomers or combinations thereof.

The number and type of carboxylic acid or ester residues present in the grafted polychloroprene polymer used in the elastomeric film-forming composition may vary, and will depend on the purpose for which the composition will be used. The number of carboxylic acid or ester residues present in the grafted polychloroprene polymer can be expressed in parts by weight of the polymer. The carboxylic acid content is not specifically limited.

In order to produce carboxylic acid- or ester-grafted polychloroprene having specific amounts of carboxylic acid or ester, the carboxylic acid- or ester-grafted polychlorobutadiene can be prepared by adjusting the amount of the carboxylic acid or ester used relative to the amount of polychlorobutadiene used to form the polymer. The amounts of carboxylic acid or ester (or the extent of grafting or the degree of carboxylation of the polymer) may be verified by determining the amount of unreacted carboxylic acid or ester using analytical methods, and subtracting this amount from the amount of carboxylic acid or ester added.

In one embodiment, the carboxylic acid- or ester-grafted polychlorobutadiene contains the carboxylic acid or ester in an amount of from 0.01% to 8% by weight of chlorobutadiene units present in the polymer. In other words, the mole ratio of chloroprene to the CO$_2$H group is 1:0.000196 to 1:0.1573, and the CO$_2$H group will be present on approximately every 6 to every 5102 moles of the chlorobutadiene units. Expressed another way, in some embodiments from 0.02% to 15% of the chlorobutadiene units in the polymer are attached to a carboxylic acid group. Preferably, the polymer contains the carboxylic acid residue or ester thereof in an amount of from about 0.5 to about 5%, about 0.5 to about 4%, about 0.5 to about 3.5%, or from about 1% to about 2.5% by weight of the chlorobutadiene units present in the polymer.

Using a carboxylic acid- or ester-grafted polychlorobutadiene having a carboxylic acid or ester group in an amount of 0.01 to 8% by weight of the chlorobutadiene units present in the polymer may provide an elastomeric film having improved properties. As one example, having carboxylic acid or ester group in an amount of 0.01 to 8% by weight of the chlorobutadiene units present in the polymer allows production of thin films, such as films having a thickness in the range of 0.01-3.0 mm, such as 0.01-2.5 mm, 0.01-2.0 mm, 0.01-1.5 mm, 0.01-1.0 mm, 0.01-0.5 mm, 0.01-0.4 mm, 0.01-0.3 mm, 0.01-0.2 mm, 0.02-0.2 mm, 0.01-0.10 mm, 0.03-3.0 mm, 0.03-2.5 mm, 0.03-2.0 mm, 0.03-1.5 mm, 0.03-1.0 mm, 0.03-0.5 mm, 0.03-0.4 mm, 0.03-0.3 mm, 0.03-0.2 mm, 0.03-0.10 mm, 0.05-3.0 mm, 0.05-2.5 mm, 0.05-2.0 mm, 0.05-1.5 mm, 0.05-1.0 mm, 0.05-0.5 mm, 0.05-0.4 mm, 0.05-0.3 mm, 0.05-0.2 mm, 0.05-0.10 mm, 0.08-3.0 mm, 0.08-2.5 mm, 0.08-2.0 mm, 0.08-1.5 mm, 0.08-1.0 mm, 0.08-0.5 mm, 0.08-0.4 mm, 0.08-0.3 mm, 0.08-0.2 mm, 0.08-0.10 mm, 0.1-3.0 mm, 0.1-2.5 mm, 0.1-2.0 mm, 0.1-1.5 mm, 0.1-1.0 mm, 0.1-0.5 mm, 0.1-0.4 mm, 0.1-0.3 mm, 0.1-0.2 mm, 0.15-3.0 mm, 0.15-2.5 mm, 0.15-2.0 mm, 0.15-1.5 mm, 0.15-1.0 mm, 0.15-0.5 mm, 0.15-0.4 mm, 0.15-0.3 mm, 0.15-0.2 mm, 0.02-0.08 mm, 0.03-0.08 mm, or 0.05-0.08 mm. As another example, having carboxylic acid or ester group in an amount of 0.01 to 8% by weight of the chlorobutadiene units present in the polymer allows production of elastomeric films having a lower modulus at 300%, a lower modulus at 500% and/or a higher elongation to break, such as a modulus at 300% of less than 660 psi, a stress at 500% of less than about 2400 psi and/or an elongation to break of greater than about 520%.

The presence of the carboxylic acid residue or ester thereof in an amount at the lower end of the above ranges results in a highly flexible or elastic elastomeric film or dipped article, however, the processability of such a composition is more complex. The presence of the carboxylic acid residue or ester thereof in an amount at the higher end of the above ranges results in a tougher elastomeric film or dipped article, however, the processability of such a composition is improved. Accordingly, a balance must be struck between the desired softness of the elastomeric film or dipped article and the processability of the composition.

The elastomeric film or dipped article made from a composition containing a carboxylic acid- or ester-grafted polychlorobutadiene having a lower amount of carboxylic acid or ester in the polymer may be suitable for use in applications such as surgical gloves, where a softer or more elastic film is able to provide the wearer with good tactile perception. For example, the carboxylic acid or ester content suitable for production of thinner, softer and more elastic films may be in the range of about 0.01 to 5.0%, such as about 0.01 to 3%, 0.01 to 2.5%, 0.01 to 2%, about 0.01 to 1.8%, about 0.01 to 1.6%, about 0.01 to 1.5%, about 0.01 to 1.4%, about 0.01 to 1.3%, about 0.01 to 1.2%, about 0.01 to 1.1%, about 0.01 to 1%, about 0.01 to 0.9%, about 0.01 to 0.8%, about 0.01 to 0.7%, about 0.01 to 0.6%, about 0.01 to 0.5%, about 0.01 to 0.4%, about 0.01 to 0.3%, about 0.01 to 0.2%, about 0.01 to 0.1% or about 0.01 to 0.05%.

The elastomeric film or dipped article made from a composition containing a carboxylic acid- or ester-grafted polychlorobutadiene having a higher amount of carboxylic acid or ester in the polymer may be suitable for use in applications such as household gloves, industrial gloves or heavy duty gloves, where a more rigid, less elastic film is required. For example, the carboxylic acid or ester content suitable for production of more rigid, less elastic or more durable films may be in the range of about 0.5 to 8%, such as about 1 to 8%, about 0.5 to 6%, about 1 to 6%, about 0.5 to 7%, about 1 to 7%, about 1.5 to 7%, about 1.5 to 6%, about 2 to 8%, about 2 to 7.5%, about 2 to 7%, about 2 to 6%, about 2.5 to 8%, about 2.5 to 7.5%, about 2.5 to 7%, about 2.5 to 6%, about 3 to 8%, about 3 to 7%, about 3 to 6%, about 4 to 8%, about 4 to 7%, about 4 to 6%, about 5 to 8%, about 5 to 7%, about 5 to 6%, about 6 to 8%, or about 6 to 7%.

Cross-Linking Agents

The carboxylic acid- or ester-grafted polychlorobutadiene can be cross-linked with one or more cross-linking agents to produce the elastomeric film. Various types of cross-linking agents can be used.

Accelerators are one sub-class of cross-linking agents which release sulphur, or act with sulphur-containing compounds, to accelerate sulphur-based covalent cross-linking of the elastomer-forming polymer. Generally, accelerators can be advantageous as they shorten the curing (vulcanisation) time, lower the curing temperature or decrease the amount of cross-linking agents required to be used in the composition. However, on the negative side, accelerators can give rise to allergic reactions, such as allergic contact dermatitis with symptoms including erythema, vesicles, papules, pruritus, blisters and/or crusting. Examples of suitable accelerators include the carbamates such as thiocarbamates (e.g. zinc dibutyl dithiocarbamate (ZDBC), Zinc diethyl dithiocarbamate (ZDEC)); thiurams (eg. tetraethylthiuram disulfide (TETD), Tetramethylthiuram disulphide (TMTD)); thiourea (Ethyl thiourea (ETU) and diphenylthiourea (DPTU); thiazoles (e.g. Mercapto Benzothiazoles (MBT), Mercapto Benzothiozole disulphide (MBTS), zinc 2-mercaptobenzothiazole (ZMBT)); guanidines (e.g. Diphenylguanidine (DPG)) and aldehyde/amine-based accelerators (e.g. hexamethylenetetramine). Other examples are well known in the art and can be obtained from various publicly available sources.

Another class of cross-linking agents are the ionic cross-linking agents, which include metal oxides, metal hydroxides and peroxides (organic and inorganic). These work by ionically cross-linking ionically-crosslinkable groups in the elastomer-forming polymer. For example, a metal oxide cross-linker can work by ionically cross-linking the carboxylic acid groups of the carboxylic acid- or ester-grafted polychlorobutadiene. Examples of suitable metal oxide cross-linking agents include the multivalent metal oxide cross-linking agents, such as lead oxide, magnesium oxide, barium oxide, zinc oxide, manganese oxide, copper oxide, aluminium oxide, nickel oxide and combinations thereof. Examples of suitable metal hydroxide cross-linking agents include zinc hydroxide, aluminium hydroxide, magnesium hydroxide, and other metal hydroxides, such as barium hydroxide, manganese hydroxide, copper hydroxide, and nickel hydroxide. An example of a peroxide cross-linking agent is 1,1-di(t-butylperoxy)-3,3,5-trimethylcyclohexane, which can be purchased under the trade name Trigonox 29-40B-pd. Other cross-linking agents that are suitable for use in the elastomeric film-forming composition are selected from, but not restricted to cross-linking monomers, reactive oligomers, polyisocyanate oligomers, functional, cross-linkable polymers, derivatives of ethylene glycol di(meth)acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrylate (TEDMA)), derivatives of methylenebisacrylamide (such as N,N.-methylenebisacrylamide, N,N.-methylenebisacrylamide, N,N.-(1,2 dihydroxyethylene)bisacrylamide), formaldehyde-free cross-linking agents (such as N-(1-Hydroxy-2,2-dimethoxyethyl)acrylamide), divinylbenzene, divinylether, diallyl phthalate, divinylsulfone and the like. Some of these cross-linking agents are commercially available and are supplied by companies such as Aldrich. Combinations of these cross-linking agents can also be used.

The amount of cross-linking agent is typically in the range 0.5-15.0 phr. In some embodiments, the amount of cross-linking agent is suitably within one of the following ranges: 0.5-15.0 phr, 1.0-15.0 phr, 1.5-15.0 phr, 0.5-13.0 phr, 1.0-13.0 phr, 1.5-13.0 phr, 0.5-11.0 phr, 1.0-11.0 phr, 1.5-11.0 phr, 0.5-10.0 phr, 1.0-10.0 phr, 1.5-10.0 phr, 0.5-8.0 phr, 1.0-8.0 phr, 1.5-8.0 phr, 0.5-7.0 phr, 1.0-7.0 phr, 1.5-7.0 phr, 2.0-8.0 phr, 2.5-10.0 phr, 5.0-10.0 phr, 3.0-7.0 phr, 3.0-6.0 phr, 4.0-7.0 phr, 4.0-6.0 phr, 4.0-5.0 phr, 2.0-5.0 phr, 2.0-4.0 phr, 3.0-4.0 phr, 6-10 phr, 7-10 phr, 6-8 phr, 5-9 phr, 8-10 phr, 0.01-3.5 phr, 0.01-3.0 phr, 0.01-2.0 phr, 0.01-1.5 phr, 0.01-1.0 phr or 0.01-0.5 phr.

A metal oxide can serve two functions in the elastomeric film-forming compositions of the present invention. Firstly the metal oxide can neutralize hydrochloric acid that is formed from the slow dehydrochlorination of the chlorobutadiene units, and secondly, the metal oxide can cross-link the functional groups to provide excellent bond strength and heat resistance. The allyl chloride structures in the carboxylic acid- or ester-grafted polychlorobutadiene function as major cross-linking sites by reaction with metal oxides. For at least this reason, ionic cross-linking agents such as metal oxides and peroxides may need to be used in higher quantities than they would typically be used. For example, in some embodiments, zinc oxide may be added in very high quantity varying from 3 to 10 parts or 5 to 10 parts per hundred parts of dry rubber. The zinc oxide requirement for other synthetic elastomers like acrylonitrile, polyisoprene and even natural rubber may be lower, for example, 2 phr or even less.

The suitable vulcanization activators comprise metal oxides, such as lead oxide, magnesium oxide, barium oxide, zinc oxide, manganese oxide, copper oxide, aluminium oxide and nickel oxide, preferably zinc oxide.

A further class of cross-linking agents are the covalent cross-linking agents, which include sulphur and sulphur-containing vulcanising agents. These work by covalently cross-linking unsaturated double bonds present in the elastomer-forming polymer. The sulphur can be present in the form of elemental sulphur. The sulphur in sulphur-containing vulcanising agents can also be donated by organic sulphuric compounds, for example TMTD (Tetramethylthiuram Disulfide). Sulphur donors or sulphur-containing vulcanising agents such as this one are likely to contribute to chemical allergies and it is preferred to keep their use to a minimum in the manufacture of gloves when allergic content is an issue. Thus, if used, the sulphur is preferably present in the form of elemental sulphur.

Generally, the amount of cross-linking determines the elasticity of the elastomeric film. Therefore, the amount and type of cross-linking agent will contribute to the extent of cross-linking and the elasticity of the final elastomeric film.

For ionic cross-linking agents such as metal oxide and peroxide cross-linking agents, when used, the amount is typically in the range 1.0-10.0 phr. The amount of metal oxide cross-linking agent is suitably within one of the following ranges: 1.0-10.0 phr, 2.0-8.0 phr, 2.5-10.0 phr, 5.0-10.0 phr, 3.0-7.0 phr, 3.0-6.0 phr, 4.0-7.0 phr, 4.0-6.0 phr, 4.0-5.0 phr, 2.0-5.0 phr, 2.0-4.0 phr, 3.0-4.0 phr, 6-10 phr, 7-10 phr, 5-8 phr, 5-6 phr, 6-8 phr, 5-9 phr, or 8-10 phr In some embodiments, where the degree of carboxylation of the polymer is lower, the amount of metal oxide used will be at the higher end of the range. For example, The amount of metal oxide cross-linking agent is suitably within one of the following ranges: 3-10 phr, 5-10 phr, 6-10 phr, 7-10 phr, 5-8 phr, 5-6 phr, 6-8 phr, 5-9 phr, or 8-10 phr. In some embodiments, where the amount of carboxylic acid or ester in the carboxylic acid- or ester-grafted polychlorobutadiene is higher, the amount of metal oxide used will be at the lower end of the range. For example, the amount of metal oxide cross-linking agent is suitably within one of the following ranges: 1.0 to 5 phr, 2.0 to 5 phr, 2.0 to 4.0 phr, 2.5 to 5 phr or 3.0 to 5.0 phr. However, the effect of the presence of additional or excess metal-oxides may be diminished or insignificant where other elastomers, such as the second elastomer, are added to the composition and blended with the polymer comprising chlorobutadiene units and one or more carboxylic acid residues or esters thereof.

Sulphur requires high energy at curing (thus high curing temperature and/or time) compared to other cross-linking agents. However, sulphur does provide the resulting dipped articles, such as gloves, with greater chemical resistance, and therefore it may be desired for this reason. The amount of sulphur is suitably within one of the following ranges: 0.0-3.5 phr, such as 0.01-3.5 phr, 0.01-3.0 phr, 0.01-2.0 phr, 0.01-1.5 phr, 0.01-1.0 phr, 0.01-0.5 phr, 0.5-3.5 phr, 0.5-3.0 phr, 0.5-2.0 phr and 0.5-1.5 phr.

In some embodiments, where the amount of carboxylic acid or ester in the carboxylic acid or ester in the carboxylic acid- or ester-grafted polychlorobutadiene is higher, it could be possible to reduce and even eliminate accelerators from the elastomeric film-forming composition of the invention. For example, for dipped articles having a larger film thickness, accelerator elimination is feasible where the strength is not compromised. However, further improved physical characteristics may be obtained using an accelerator, such as further improved softness. Where this property is desirable, it will be preferable to use sufficient accelerators. Accordingly, the composition for producing the elastomeric film will be accelerator-free in some embodiments, and will further comprise an accelerator in other embodiments.

The amount of accelerator is suitably between 0.1-2.0 phr, such as between 0.1-1.5 phr, 0.1-1.0 phr, 0.2-1.0 phr, 0.3-2.0 phr, 0.3-1.5 phr, 0.2-0.6 phr, 0.5-2.0 phr, or 0.5-1.5 phr. Suitable accelerators include mercaptobenzothiazoles and derivatives thereof, dithiocarbamates and derivatives thereof, sulphur donors, guanidines, thio-urea and aldehyde-amine reaction products.

In some embodiments, the composition will be free of a hardening amount of a hardener. Hardeners are often used in adhesive compositions to harden the adhesive when it is mixed with other components such as resins. The composition of the invention may be used in the preparation of films and dipped articles, such as gloves. In some embodiments, the composition of the invention may be used to form dipped articles such as gloves which are elastic. The addition of a hardener would result in formation of elastomeric films which are hard or stiff and may in some cases be brittle.

In one embodiment, the cross-linking agents used in the elastomeric film-forming composition of the present invention are selected from the group consisting of sulphur, a sulphur-containing vulcanising agent, organic peroxide, metal oxide, metal hydroxide and combinations thereof. Preferably, the composition contains a combination of sulphur or a sulphur-containing vulcanising agent, and a metal oxide or metal hydroxide. The use of the combination of cross-linking agents, such as sulphur and metal oxide, provides a polymer having ionic cross-linking as well as covalent cross-linking across the unsaturated double bonds of the carboxylic acid- or ester-grafted polychlorobutadiene. The metal oxide will form ionic bonds to the carboxylic acid or ester groups and to the chlorine in the polymer. Formation of ionic bonds requires less energy and allows quicker production of the elastomeric film-forming composition. The sulphur will form covalent bonds with the butadiene, particularly at carbon sites. Formation of these covalent bonds requires higher energy, however, the resulting elastomeric film may have improved permeation characteristics. Accordingly, the combination of these types of cross-linking agents provides a balance between the time and energy required to produce the elastomeric film and the performance of the elastomeric film. The combination of ionic and covalent cross-linking in the polymer may also provide an elastomeric film having improved properties, such as improved strength and durability of the film. The amount and type of cross-linking also contributes to the elasticity of the film.

Second Elastomer

The carboxylic acid- or ester-grafted polychlorobutadiene may be blended with one or more alternative elastomers also referred to as a second elastomer. For example, the alternative elastomers may be lower cost elastomers, which are added in order to reduce the cost of the end product. The type and amount of the one or more second elastomers added to the elastomeric film-forming composition will depend on the carboxylic acid- or ester-grafted polychlorobutadiene used in the composition, and the intended use of the composition.

Examples of suitable second elastomers include synthetic elastomers or synthetic rubbers such as nitrile rubber, styrene butadiene rubber, butyl rubber, polyisoprene, polychloroprene, polybutadiene, polyvinylchloride, polyurethane, styrene diblock copolymers, styrene triblock copolymers, acrylic polymers or other synthetic elastomers or mixtures thereof. The second elastomer may be carboxylated (for example, by grafting or copolymerizing and or mixtures thereof), non-carboxylated or a mixture of carboxylated and non-carboxylated elastomers, or a mixture of elastomers having varied degrees of carboxylation.

In some embodiments, the amount of the second elastomer would not exceed 95% of the polymer component of the elastomeric film-forming composition on a dry basis. The polymer component of the elastomeric film-forming composition includes the amount of the carboxylic acid- or ester-grafted polychlorobutadiene and the amount of the second elastomer. For example, the amount of the second elastomer may be in the range of from 0 to 95% of the polymer component of the elastomeric film-forming composition on a dry basis, such as about 5-95%, 0-65%, 0-50%, 5-65%, 10-95%, 10-65%, 15-95%, 15-65%, 20-95%, 20-65%, 25-95%, 25-65%, 30-95%, 30-65%, 35-95%, 35-65%, 40-95%, 40-65%, 50-60%, 50-65%, 50-95%, 60-65%, 60-75%, 60-80%, 60-95%, 70-90%, 70-95%, 80-95%, 0-5%, 5-10%, 10-15%, 15-20%, 20-25%, 25-30%, 30-35%, 35-40%, or 40-50%.

It will be appreciated that the blended composition will retain the favourable properties provided by the use of the carboxylic acid- or ester-grafted polychlorobutadiene. Preferably, the amount of the second elastomer is less than about 75% of the polymer component of the elastomeric film-forming composition on a dry basis, such as 0-75%, less than 65%, 0-65%, 5-75%, 5-65%, 10-75%, 10-65%, 15-75%, 15-65%, 20-75%, 20-65%, 25-75%, 25-65%, 30-75%, 30-65%, 35-75%, 35-65%, 40-75% or 40-65%.

In some embodiments, the amount of the second elastomer may depend on the amount of carboxylic acid or ester in the carboxylic acid- or ester-grafted polychlorobutadiene. A balance must be struck between the amount of carboxylic acid or ester in the carboxylic acid- or ester-grafted polychlorobutadiene and the amount of the second elastomer that is used in the composition in order to produce an elastomeric film or dipped article (such as a glove) having a suitable thickness, a suitable amount of material used to form the film or article, and having suitable properties for its use. Accordingly, the amount of the second elastomer used will depend on the carboxylic acid- or ester-grafted polychlorobutadiene that is used and the end product to be produced.

As one example, a more rigid, less elastic or more durable film may be produced when a high amount of carboxylic acid or ester is present in the carboxylic acid- or ester-grafted polychlorobutadiene and the amount of the second elastomer used in the composition is towards the upper end of the range of 0-95% of the polymer component of the elastomeric film-forming composition on a dry basis. For example, when the carboxylic acid or ester content is in the range of about 1 to 8%, the amount of the second elastomer may be within one of the following ranges: 50-60%, 50-65%, 50-95%, 60-65%, 60-75%, 60-80%, 60-95%, 70-90%, 70-95%, 80-95%, or 0-50%.

As another example, a softer, more elastic film may be produced when a low amount of carboxylic acid or ester is present in the carboxylic acid- or ester-grafted polychlorobutadiene and the amount of the second elastomer used in the composition is towards the lower end of the range of 0-95% of the polymer component of the elastomeric film-forming composition on a dry basis. For example, when the carboxylic acid or ester content is in the range of about 0.01 to 5%, the amount of the second elastomer may be within one of the following ranges: 0-5%, 5-10%, 10-15%, 15-20%, 20-25%, 25-30%, 30-35%, 35-40%, 40-50%, or 50-95%.

Other Components or Additives

Other components or additives may be included in the composition can include one or more additives selected from the group consisting of plasticizers, antiozonants, stabilisers such as pH stabilisers, emulsifiers, antioxidants, vulcanising agents, polymerisation initiators, pigments, fillers, colourising agents and sensitisers.

Stabilisers may be used in the elastomeric film-forming composition. The stabilizer may be, for example, an oleate, stearate or other non-ionic surfactants. The elastomer-forming polymer can be diluted with a solution of a stabilizer, such as potassium hydroxide, ammonium hydroxide and/or sodium hydroxide. The amount of stabiliser used is dependent on the polymer used in the elastomeric film-forming composition, the pH of the composition and other factors. The stabiliser can range from 0.1-5.0 phr, e.g. 0.5 to 2 phr, preferably 1.0 to 1.5 phr, which is diluted with water, preferably filtered water or de-ionized water, or water having a total solid content of around 5 ppm level—water.

Emulsifiers may be used in the elastomeric film-forming composition. Suitable emulsifiers include sodium alkyl sulphates or other non-ionic and ionic surfactants. The amount of emulsifier used is dependent on the on the polymer used in the elastomeric film-forming composition, the pH of the composition and other factors. The amount of emulsifier can range from about 0.1 to 5 phr, 0.5 to 5 phr, 0.1 to 3 phr or 0.5 to 3 phr.

pH stabilisers may be used to avoid the possibility of destabilization, which is possible where the elastomer-forming polymer contains carboxylic acid groups. Suitable pH stabilisers include potassium hydroxide, ammonium hydroxide and/or sodium hydroxide. Preferably, the pH stabiliser is potassium hydroxide. A diluted stabilizer solution can be mixed with the elastomer-forming polymer. The pH of the mixture is suitably adjusted to between about 8.5 to about 13.5, or between about 8.5 to about 11.0. The cross-linking agent(s) can then be added to the mixture. The amount of pH stabilizer can range from about 0.1 to 3.0 phr, 0.1 to 2.5 phr, 0.1 to 2.0 phr, 0.1 to 1.5 phr, 0.1 to 1.0 phr, 0.1 to 0.5 phr, 0.2 to 3.0 phr, 0.2 to 2.5 phr, 0.2 to 2.0 phr, 0.2 to 1.5 phr, 0.2 to 1.0 phr, 0.2 to 0.5 phr, 0.5 to 3.0 phr, 0.5 to 2.5 phr, 0.5 to 2.0 phr, 0.5 to 1.5 phr or 0.5 to 1.0 phr.

Antiozonants may be used in the elastomeric film-forming composition. Suitable anitozonants include paraffinic waxes, microcrystalline waxes and intermediate types (which are blends of both paraffinic and microcrystalline waxes). The amount of antiozonant can range from about 0.1 to 5.0 phr, 0.1 to 3.0 phr, 0.1 to 1.5 phr, 0.5 to 5.0 phr, 0.5 to 3.0 phr, or 0.5 to 1.5 phr.

Antioxidants may be added to the elastomeric film-forming composition of the present invention. Suitable antioxidants include hindered arylamines or polymeric hindered phenols, and Wingstal L (the product of p-cresol and dicyclopentadiene). The antioxidant may, for example, be added in an amount ranging from about 0.1-5.0 phr, such as 0.1-3.0 phr, 0.5-3.0 phr, 0.1-1.5 phr, 0.1-1.0 phr or 0.3-0.5 phr.

Pigments, such as titanium dioxide, are selected for their pigmentation, or to reduce the transparency of the final elastomeric film. Pigments may also be referred to as opaqueness providers. The amount of pigment may, for example, be added in amounts ranging from about 0.01-10.0 phr, such as 0.01-5.0 phr, 0.01-3.0 phr, 0.01-2.0 phr, 0.01-1.5 phr, or 1.5-2.0 phr and colorants can also be added in the desired amounts. The mixture is then diluted to the target total solids concentration by the addition of a liquid, such as water. The pigments used in the elastomeric film-forming composition may be selected from the group consisting of EN/USFDA approved dyes.

Rubber reodorants may be used in the elastomeric film-forming composition. Suitable rubber reodorants include perfume oils of natural or synthetic origins. The amount of rubber reodorant can range from about 0.001 to 2.0 phr.

Wetting agents may be used in the elastomeric film-forming composition. Suitable wetting agent emulsifiers include anionic surfactants like sodium dodecyl benzene sulphonate or sodium lauryl ether sulphate, or non-ionic ethoxylated alkyl phenols such as octylphenoxy polyethoxy ethanol or other non-ionic wetting agents. The amount of wetting agent can range from about 0.001 to 2.0 phr.

Defoamers or anti-foam may be used in the elastomeric film-forming composition. Defoamers may be chosen from naphthalene type defoamers, silicone type defoamers and other non-hydrocarbon type defoamers or defoamers of refined vegetable origin. The amount of defoamers can range from about 0.001 to 2.0 phr, such as about 0.001-1.0 phr, 0.001-0.1 phr, 0.001-0.01 phr.

The carboxylic acid- or ester-grafted polychlorobutadiene could also be blended with an inorganic filler. Suitable inorganic fillers include calcium carbonate, carbon black or clay. Preferably, the amount of inorganic filler included in the blend would not exceed 30% either alone or in combination. It will be appreciated that the blended composition will retain the favourable properties provided by the use of the carboxylic acid- or ester-grafted polychlorobutadiene.

Sensitisers are chemicals that can be used in compositions for producing elastomeric films to control the amount of the composition that will remain coated on the mould during dipping. Examples of sensitisers known in the art that can be used in the composition for producing an elastomeric film include polyvinyl methylether, polypropylene glycol, ammonium nitrate and ammonium chloride. When used, the amount of sensitiser will be chosen based on the desired film thickness to remain on the mould during dipping, and will generally be between 0.01-5.0 phr. For thinner films, the amount will generally be between about 0.01 to 2.0 phr, such as, about 0.1 to 1.0 phr. When other techniques are used for controlling the film thickness on the mould, such as the use of pre-dipping the mould into coagulant before undertaking the multiple dipping into the composition for producing the elastomeric film, the composition for producing an elastomeric film may not comprise a sensitiser.

In some embodiments, the composition will be free of a tackifier. Tackifiers are often used in adhesive compositions, particularly pressure sensitive adhesives, to improve the stickyness of the adhesive or the ability of the adhesive to form an immediate bond with a surface upon contact. Tackifiers are usually resins, such as rosins and their derivates, terpenes and modified terpenes, aliphatic, cycloaliphatic and aromatic resins, hydrogenated hydrocarbon resins, terpene-phenol resins or mixtures thereof. The composition of the invention may be used in the preparation of films and dipped articles, such as gloves. The addition of a tackifier would result in formation of sticky elastomeric films which are not suitable for use in articles, such as gloves.

Those skilled in the art will readily be able to vary the components of the elastomeric film-forming composition to suit the particular polymer used as well as the particular final article desired. It will also be understood by those of skill in the art that specific chemicals or compounds which have been listed above are intended to be representative of conventional materials that may be used in formulating the elastomeric film-forming composition and are merely intended as non-limiting examples of each such component of the composition.

Preparation of the Elastomeric Film-Forming Composition

The composition for producing an elastomeric film can be prepared by mixing the carboxylic acid- or ester-grafted polychlorobutadiene with one or more cross-linking agents, optionally one or more additives and optionally a second elastomer, in a liquid (e.g. water). As described above, the carboxylic acid- or ester-grafted polychlorobutadiene or the polymer in combination with the other components are diluted with a liquid to reach the desired total solids content of the composition.

Suitable additives or other components as described above may be included in the composition, and may be added to the polymer before addition of the cross-linking agent, or added to the mixture of the polymer and the cross-linking agent.

The preparation of the composition includes steps known in the art, and the composition can be prepared in a conventional manner.

Typically, the powder components of the composition will be combined and milled using suitable milling equipment to reduce the particle size to a suitable range. Preferably, the average particle size is below 5 microns. Uniform particle size is desirable, and coarse milling may result in non-uniform particles and therefore a non-uniform film, which can result in high fluctuation in film properties.

When used, the surfactant and the pH stabilizer are added to the liquid (e.g. water) and mixed properly without any foam formation. This liquid is then used to dilute the polymer or a blend of the polymer with a second elastomer, and other additives or components to the desired total solids content. The total solids content of the elastomeric film-forming composition will depend on the planned film thickness.

The pH of the dispersion may then be adjusted as necessary, preferably to a pH within the range of 8.5 to 13.5 (e.g. a pH above 9 or preferably a pH between 10 and 11). Any high variation between the diluted polymer and dispersion will result in coagulation from the micro level to the macro level.

When the components have been mixed uniformly or to homogeneity, other additives such as colorants and emulsifiers are added. The elastomeric film-forming composition is then left for maturation. The length of the maturation may vary depending on the level of cross-linking agent and the degree of carboxylation of the polymer. Generally, the composition will be left for a minimum of 12 to 18 hours, while in some cases maturation could be conducted over a period of days depending upon the requirements for preparing the dipped article and the level of cross-linking agents present. The compounded elastomeric film composition with suitable additives could be prematured by holding the composition at a controlled elevated temperature. For example, the elastomeric film composition could be held at 20° C. to 60° C. for a period of, for example, about 4 hours to about 24 hours depending on the temperature, degree of carboxylation of the polymer, the amount and type of vulcanization activators and accelerators, and type and quantity of pH stabilizer and emulsifier stabilizer and wetting agents/surfactants.

Preparation of the Elastomeric Film

The manufacture of the elastomeric film may use conventional equipment.

Optional Step (a) Dipping the Former into a Coagulant

A suitable former, which is based on the shape of the article to be produced (e.g. flat for a film or glove-shaped for a glove) can be dipped into a coagulant. The cleanliness of the former is an important aspect with respect to the pin hole formation in the elastomeric film or the cleanliness of the elastomeric film. Hence the former, which is normally made of a ceramic material, will be serially dipped in mild acid solutions, water, and/or alkaline solutions, and passed through brushes and hot water. The sequence could be altered depending on the cleaning requirements. In some embodiments, cleaning of the former involves dipping the former in acid solutions and alkaline solutions.

Following cleaning, the former is passed through a dryer so that the adhering water is removed by evaporation. The dryer temperature is typically above 105° C. and could be adjusted according to the line speed and oven length. It is preferable the former is dry before entering the next station.

The former, dried as described above, is then dipped into a coagulant leaving a thin coating of the coagulant on the surface of the former. In some embodiments, the coagulant is a salt solution containing ions. In this embodiment, dipping the former into the coagulant leaves a thin coating of the charged ions on the surface of the former. The charged ion coating can assist in controlling the amount composition for forming the elastomeric film that will subsequently remain on the surface of the former after dipping into the composition, through charge interactions.

The ions may be cationic (as in the case of, for example, sodium ion-containing coagulants or calcium ion-containing coagulants) or anionic, and the choice will be based on the identity of the elastomeric polymer. In some embodiments, the coagulant will have a pH greater than 7, such as pH 8 to 10.

Generally metal ion solutions containing cations are suited to a broad range of elastomeric polymers. Examples of such metal salt ions are sodium, calcium, magnesium, barium, zinc, and aluminium. The counter ions may be halides (such as chloride), nitrate, acetate or sulphate, amongst others. In the case of calcium ion-containing coagulants, the calcium ions can be provided as a solution of calcium nitrate or calcium chloride.

The coagulant may also include any other agents, such as wetting agents (such as fatty alcohol ethoxide or other suitable surfactants), anti-tack agents, anti-foaming agents and/or mould release agents, such as silicon emulsions, polymer release agents and metallic stearates, examples of which are zinc, calcium and potassium stearates.

The concentration of ions in the coagulant can broadly be in the range of 0.0-50% by weight of the coagulant solution (measured as the compound of the multivalent ion in the solution of the multivalent ions), depending on the desired thickness of the elastomeric film layers and the number of layers to be applied (i.e. one layer or two or more layers). In the case of thinner layers, the concentration is suitably in the range of 0.0-20%, 0.0-15%, 0.0-12%, 1.5-20%, 1.5-15%, 1.0-10%, 1.5-10%, 4-10%, 5-10%, 5-35%, 10-30%, 7-40%, 8-50% and 5-45%. Preferably, the concentration is in the range of 10-30%. The amounts of other components such as wetness and anti-tack agents are dependent on the properties desired through the use of these agents, and will vary accordingly.

The coagulant may also include metallic stearates in a concentration in the range of about 0.1-5.0% by weight, suitable wetting agents in a concentration in the range of about 0.001-1.0%, and/or antifoaming agents in a concentration in the range of 0.001-1.0% by weight.

The duration or dwell time for the mould in the coagulant is suitably between 1 and 30 seconds. In some embodiments, the dwell time for the mould in the coagulant is 1 to 10 seconds. In some embodiments, the dwell time for the mould in the coagulant may be longer than 30 seconds. The temperature of the coagulant into which the mould is dipped may, for example, be between 30° C.-80° C.

Prior to dipping the former into the coagulant, the former may be subjected to heating. The heating may form a part of a preliminary mould washing and drying procedure.

The mould may in this case be heated to a surface temperature in the range of 25° C. to 85° C., for example a temperature in the range of 30° C. to 70° C.

Optional Step (b) Drying or Partially Drying the Coagulant-Dipped Former

If the former is dipped into a coagulant, following this step the former is dried or partially dried.

Drying (or partial drying) is a step that may be repeated in several stages during the production of the multi-layered elastomeric film or dipped article. At each drying or partial drying step, the drying may be performed by any suitable technique or equipment known in the art, including the application of hot air or radiant heat, or a drying radiation source such as infra-red (IR) and far IR radiation. This can be performed in an oven or any other suitable drying equipment or environment. In the case of drying in an oven, or under the influence of hot air or radiant heat, the former may be passed through the drying zone, which applies heat at an elevated temperature, for a period of time that is sufficient to drive off the excess moisture/liquid to a sufficient degree of dryness. In the case of drying the coagulant remaining on the former, the drying zone (such as oven) may for example be held at, or apply, heat at a temperature of between 50° C.-250° C. Typically, the temperature is maintained above 105° C. to enable water evaporation. In some embodiments, the temperature is maintained at from about 110° C. to about 130° C. Depending on the method used for drying, the temperature may be adjusted according to factors such as line speed, the length of the drying zone and the drying time.

The former typically remains in this zone (or progresses through this zone) for a period of time sufficient to reach the target level of drying, and optionally a target surface temperature of the coagulant on the former. This may be between 25° C.-85° C., for example between 40° C.-70° C.

The surface temperature of a coating on the former (in this case, the coagulant) can be tested by any suitable technique. One example involves the use of a device to measure the surface temperature of an object by the infra-red energy emitted by the object. An example of a device of this type is the Thermo-Hunter, model: PT-2LD produced by Optex Co. Ltd. Other techniques for measuring the surface temperature of the film are known in the art.

Step (i) Dipping the Former into the Elastomeric Film-Forming Composition of the Invention to Produce a Layer of Elastomeric Film-Forming Composition on the Former Prior to the step of dipping the former into the elastomeric film-forming composition, the elastomeric film-forming composition may be seasoned or matured in a holding tank.

As described above, the length of the maturation may vary depending on the level of cross-linking agent and the degree of carboxylation of the polymer. Generally, the composition will be left for a minimum of 12 to 18 hours, while in some cases maturation could be conducted over a period of days depending upon the requirements for preparing the dipped article and the level of cross-linking agents present. The elastomeric film-forming composition together with any suitable additives could be prematured by holding the composition at a controlled elevated temperature. For example, the elastomeric film-forming composition could be held at 20° C. to 60° C. for a period of, for example, about 4 hours to about 24 hours depending on the temperature, degree of carboxylation of the polymer, the amount and type of vulcanization activators and accelerators, and type and quantity of pH stabilizer and emulsifier stabilizer and wetting agents/surfactants.

The former is dipped into the composition for producing an elastomeric film, embodiments of which have been described in detail above.

The former is in the dipping tank for an amount of time to ensure the former is evenly coated, but not so long as to develop a thicker coating than necessary. Depending on the required thickness of the coating, the dwell time of the former in the dipping tank may be between about 1-60 seconds, such as between about 5 to 60 seconds, 1 to 30 seconds, 1 to 10 seconds or 2.0 to 7.0 seconds.

The temperature of the composition into which the former is dipped is generally within the range of 10° C. to 60° C., such as 10° C. to 50° C., 15° C. to 50° C., 20° C. to 50° C., 25° C. to 50° C., 25° C. to 45° C., 20° C. to 40° C. or 20° C. to 35° C. Preferably, the composition into which the former is dipped is constantly cooled with chilled water and the latex bath temperature is kept between 20-35° C., such as 20° C. to 30° C. and more preferably at 25° C. In some embodiments, the composition is constantly circulated in the tank to avoid creaming and settling of the chemicals contained in the elastomeric film-forming composition.

Preferably, the surface temperature of the former does not exceed the temperature of the elastomeric film-forming composition by more than 80° C. It has been found by the applicant that if the surface temperature of the former is more than 80° C. higher than the temperature of the composition for producing an elastomeric film, shrinkage of the coating of elastomeric film-forming composition on the former may occur. In some embodiments, the surface temperature of the former is lower than the temperature of the elastomeric film-forming composition. However, typically, the surface temperature of the former is about 20° C. to 60° C. higher than the temperature of the elastomeric film-forming composition.

Step (ii) Drying or Partially Drying the Layer of Elastomeric Film-Forming Composition on the Former The coagulated wet film is partially air dried so that the wet film get some strength before entering to the series of pre-leach tanks where ambient water or heated water (preferably around 50° C.) is continuously replenished to scavenge out the extractable surfactants and other soluble chemicals including nitrates.

The coating or layer of elastomeric film-forming composition on the mould is then dried or partially dried, to reduce the water content of from zero to above 22%. When the elastomeric film-forming composition is partially dried, it may have a water content in excess of 22% by weight, between 22% and 80%, for example, to 25% to 75%, 30% to 77% or 25% to 60%.

The drying or partial drying may be conducted using the same type of drying technique as described above in relation to step (b), using conditions necessary to reach a state of complete or partial dryness.

The drying or partial drying may be performed by any suitable technique or equipment known in the art, including the application of hot air or radiant heat, or a drying radiation source such as infra-red (IR) and far IR radiation. This can be performed in an oven or any other suitable drying equipment or environment.

When drying in an oven, or under the influence of hot air or radiant heat, the former bearing the layer or coating of elastomeric film-forming composition may be passed through the drying zone, which applies heat at an elevated temperature, for a period of time that is sufficient to drive off some or all of the excess moisture/liquid to a sufficient degree of complete or partial dryness. In this case, the drying zone (such as oven) may be held at, or apply, heat at a temperature of between about 50° C. to about 300° C., such as about 100° C. to about 300° C. (depending on the drying time). Depending on the method used for drying, the temperature may be adjusted according to factors such as line speed, the length of the drying zone and the drying time.

The drying time period may be between 2-300 seconds (depending on the temperature of the oven). Generally, the higher the oven temperature, the shorter the time period in the drying zone, and vice versa.

Generally, during drying, the former remains in the drying zone (or progresses through this zone) for a period of time sufficient to raise the surface temperature of the layer of elastomeric film-forming composition on the former to a maximum temperature between about 25° C. and about 85° C., for example, about 40° C. to about 80° C. If a higher surface temperature is reached, excessive or uneven drying may occur. In addition, the elastomeric film-forming composition on the former may require cooling prior to the next dipping step. An additional cooling step may result in delays or additional costs in the manufacture of the elastomeric film or article.

The surface temperature of the elastomeric film-forming composition on the former can be measured using the same techniques described above with respect to the coagulant layer surface temperature.

The drying or partial drying is required to reduce the water content of the elastomeric film-forming composition on the former. The water content of the dried or partially dried elastomeric film-forming composition is from zero to greater than 22%, such as between 22% and 80%, 25% to 75%, 30% to 75% or 25 to 60%. The water content of the elastomeric film-forming composition on the former can be determined by measuring the mass of a sample product at the point of completion of the partial drying step, and then driving off the remaining moisture/liquid in the sample product to obtain the dry mass of the product, and determining from these two values the total water content. Thus, if the single-layered product at this point in time weighs 100 mg, and the dried product weighs 90 mg, the water content is 10%.

The method of the present invention encompasses the preparation of single-layered or multiple-layered elastomeric films. Therefore, in some embodiments, the method may include step (v), which involves drying and curing the layered elastomeric film on the former directly after this step to prepare a single layered elastomeric film. In other embodiments, the method may include a number of repetitions of optional steps (iii) and (iv) after this step to produce a multiple-layered elastomeric film.

Step (iii) Optionally Dipping the Former Coated with the Dried or Partially Dried Layer of Elastomeric Film-Forming Composition into the Elastomeric Film-Forming Composition to Produce a Further Layer of Elastomeric Film-Forming Composition on the Former The former coated with the dried or partially dried layer of elastomeric film-forming composition is optionally dipped into an elastomeric film-forming composition. The composition into which the former is dipped can be the same as or different to the composition used to form the first layer. The composition may differ with respect to the identity (inclusive of blending ratios and extent of carboxylation level) and/or amount of the elastomer-forming polymer, the identity and/or amount of any cross-linking agent, the identity and/or amount of other additives, and the total solids content. In some embodiments, the identity of the elastomer-forming polymer in the second composition is the same as that used in the first composition. In such embodiments, the amount of the cross-linking agent is also typically the same. In other embodiments, the identity of the elastomer-forming polymer of the second composition is different to that in the first composition. The total solids content of the second composition may be the same or different to that of the first composition. The total solids content will depend in part on the desired thickness of the second (or further) layer being applied.

The dwell time of the former in the second composition is, for example, between 1 and 90 seconds, such as between 1 and 30 seconds, 5 and 90 seconds, 1 and 60 seconds, 5 and 60 seconds, 1 and 20 seconds, 1 and 10 seconds, or 2 and 5 seconds.

The temperature of the composition into which the mould is dipped is generally within the range of 10° C. to 60° C., such as 10° C. to 50° C., 15° C. to 50° C., 20° C. to 50° C., 25° C. to 50° C., 25° C. to 45° C., 20° C. to 40° C. or 20° C. to 35° C. Preferably, the composition into which the former is dipped is constantly cooled with chilled water and the latex bath temperature is kept between 20° C. to 40° C., 20° C. to 35° C., 20-30° C. or 25-40° C., more preferably at 25° C. In some embodiments, the composition is constantly circulated in the tank to avoid creaming and settling of the chemicals contained in the elastomeric film-forming composition.

Preferably, the surface temperature of the dried or partially dried layer of elastomeric film-forming composition on the former does not exceed the temperature of the composition for forming an elastomeric film by more than about 80° C. It has been found by the applicant that if the surface temperature is more than about 80° C. higher than the temperature of the composition for forming an elastomeric film, shrinkage of the elastomeric film-forming composition on the former may occur. In some embodiments, the surface temperature is lower than the temperature of the composition for forming an elastomeric film. However, typically, the surface temperature is about 20° C. to 60° C. higher than the temperature of the composition for forming an elastomeric film.

Step (iv) Optionally Repeating the Drying or Partial Drying Step (ii) and the Further Dipping Step (iii)

The drying or partial drying step and further dipping steps may be repeated. These steps are suitably repeated at least once, and may be repeated multiple times. For each repeated step, the conditions may be different compared to the original partial drying conditions and dipping conditions for producing the second layer. Thus, as an example, extent of drying, and/or the total solids content of the composition for forming an elastomeric film may differ for each layer.

For each drying step, the layer of elastomeric film-forming composition on the former is dried or partially dried to reduce the water content of the elastomeric film-forming composition such that water content of the partially dried layer of elastomeric film on the former has a water content of from zero to greater than 22%. This water content is measured by reference to the water content of the entire elastomeric film layer on the mould (that is, the elastomeric film layer formed by multiple dipping). When the elastomeric film-forming composition is partially dried, it may have a water content in excess of 22% by weight, between 22% and 80%, for example, to 25% to 75%, 30% to 77% or 25% to 60%.

The drying or partial drying may be conducted using the same type of drying technique as described above in relation to step (b), using conditions necessary to reach a state of complete or partial dryness.

After the final layer of elastomeric film-forming composition has been applied to the former, the elastomeric film-forming composition may be dried, rather than partially dried. This final drying step is described below at Step (v).

The drying or partial drying step (ii) and the further dipping step (iii) will be repeated until the film has a sufficient number of layers, where each layer is produced by a separate dipping step. The further dipping step may be conducted using the same technique as described above in relation to step (a), using conditions necessary to reach a suitable layer of elastomeric film on the former.

The composition into which the former is dipped can be the same as or different to the composition used to form the first layer or the preceding layer. The composition may differ with respect to the identity (inclusive of blending ratios and extent of carboxylation level) and/or amount of the elastomer-forming polymer, the identity and/or amount of any cross-linking agent, the identity and/or amount of other additives, and the total solids content. In some embodiments, the identity of the elastomer-forming polymer used in the further dipping step is the same as that used to form the preceding layer. In such embodiments, the amount of the cross-linking agent is also typically the same. In other embodiments, the identity of the elastomer-forming polymer used in the further dipping step is different to that used to form the preceding layer. The total solids content of the composition used in the further dipping step may be the same or different to that of the composition used to form the preceding layer. The total solids content will depend in part on the desired thickness of the further layer being applied.

In the case where multiple layered elastomeric films are prepared, at least one layer of the elastomeric film will be made from an elastomeric film-forming composition comprising a carboxylic acid- or ester-grafted polychlorobutadiene and one or more cross-linking agents. The other layers of the elastomeric film may be made from an elastomeric film-forming composition of the invention or an elastomeric film-forming composition comprising other elastomers or blends of other elastomers.

The average thickness of each layer is typically between 6% and 90% of the final elastomeric film, with some layers (such as the first layer) suitably being between 30 to 70%, or 40 to 65% of the full film thickness. The average thickness of each layer is dependent on the number of layers of composition forming the final elastomeric film. The final elastomeric film can, for example, consist of 1 to 15 layers. In some embodiments, the elastomeric film consists of 1 to 15 layers, 2 to 14 layers, 1 to 13 layers, 2 to 12 layers, 3 to 15 layers, 1 to 11 layers, 2 to 10 layers, 3 to 11 layers, 6 to 10 layers, 8 to 12 layers, 10 to 15 layers, 1 to 9 layers, 2 to 8 layers, 3 to 7 layers, 4 to 8 layers, 1 to 6 layers, 2 to 5 layers, 2 to 6 layers, 3 to 6 layers, 1 to 5 layers, 1 to 4 layers, 1 to 3 layers, or 1 to 2 layers.

Generally, although not always, the greater the number of layers in the film, the lower the % TSC of the composition for producing each subsequent layer. This is to keep the thickness of the multilayer film to a minimum. After the first layer, the % TSC of the composition used to produce each subsequent layer may be in the range 5%-50% TSC, such as 5-48% TSC, 5-45% TSC, 5-30% TSC, 5-12% TSC, 10-30% TSC, 10-40% TSC, 10-50% TSC, or 10-20% TSC.

Each layer can be of approximately equal thickness, or of differing thickness. For example the $1^{st}$ layer can be 50%, 2nd layer 30%, 3rd layer 20% for a 3-layer film. Approximately equal thickness can be achieved by varying the total solids content of the composition of each layer and the temperature at which the layer is deposited. Different mechanisms of deposition can occur for each layer and different thicknesses can be deposited even if the % TSC is maintained at the same level. Accordingly, varying the % TSC is sometimes required to maintain the same level of thickness. The thickness of the deposited layers can also vary according to the concentration of ions in the coagulant solution, or the amount of any sensitiser present in the composition for producing the elastomeric film temperature of the composition, and dwelling time of the mould into the composition.

Optional Additional Steps Prior to Drying and Curing

Further steps can be taken to fine-tune the manufacture of the elastomeric film or article. The film or article can be leached to remove extractable components. Suitable conditions for leaching extractable components from the film or article can involve contacting the film or article with heated water (e.g. through immersion) at a temperature between ambient temperature to 80° C., such as 40 to 80° C. or ambient temperature to 55° C. Leaching may be conducted for a time period of between 1 to 50 mins. During this leaching process, a substantial amount of soluble and extractable components (such as surfactant, ionic compounds) can be removed. Then leached film may subsequently be dipped into an acrylate/acrylic/urethane polymer (or other suitable coating material) solution. The purpose of this coating is to make the donning side of the article tack free. Preferably, the strength of the acrylate/acrylic/ureathane polymer (or other suitable coating material) solution is about 1-10% w/w.

In the case of glove manufacture, the glove can be subjected to beading/cuffing to create a bead or cuff at the wrist end of the glove. The beaded glove may then pass through a set of long vulcanizing ovens with various temperature zones to evaporate the water in the film and enable better cross linking. Preferably, the temperature zones are maintained at 100-150° C. Vulcanization may be conducted for a time period of between 1 to 50 minutes, or about 15 to 30 minutes depending on the film thickness.

Step (v) Drying and Curing the Layered Elastomeric Film on the Former

After the required number of layers of film have been added by one or more iterations of dipping and drying or partial drying steps, the film or article is then dried and cured. This step can be effected in an oven with a minimum temperature of 80° C., in the range 80-150° C., such as or 80-120° C., or a minimum temperature of 90° C. (such as 90-150° C. or 90-120° C.) at a minimum time of 10 minutes, in the range 10-60 minutes or about 15 to 120 minutes. Other drying and curing techniques that can be used includes UV curing. In the case of glove manufacture, the resulting glove may be tumbled using hot air at a temperature of around 40-120° C. for about 10 to 120 minutes.

Optional Additional Steps Following Drying and Curing

The film or article is stripped from the former at the conclusion of the formation process.

The film or article can be subjected to one or more further process steps prior to stripping of the film or article from the former. These optional steps include cooling, chlorination, post-curing rinsing, polymer coating, powder coating and additional drying steps.

In some embodiments, a chlorination step is used to cap the polymers and/or to decrease the tackiness of the film or article. In these embodiments, the film or article can be chlorinated on line in a chlorination chamber. A solution of 200-1500 ppm of free chlorine, or 800-1000 ppm of free chlorine may be used. The chlorination process may be carried out over a period of between about 20-60 seconds, or for about 25 seconds. The longer the chlorination process, the lower the concentration of chlorine required in the chlorination process. The chlorinated film will typically be neutralized and washed before being dried, cured and vulcanized.

The cured film may also be post-leached in hot water and optionally dipped in lubricant solution or any silicone free polymers to enable easy stripping and better donning. For surgical gloves or other specialty gloves which require specific attributes with respect to donning post processing, further specific steps may be required.

It will be appreciated that minor alteration could be made to the above to achieve the required results in terms of film quality, donning, colour, physical property and other quality characteristics etc.

Dipped Articles and Use of the Elastomeric Film-Forming Composition

The elastomeric film-forming composition of the present invention can be used to prepare a variety of dipped articles. Examples of possible dipped articles include surgical gloves and medical examination gloves, industrial gloves, finger cots, catheters, tubing, protective coverings, balloons for catheters, condoms and the like. Preferably, the elastomeric film-forming composition is used in the manufacture of gloves, such as powder-free gloves.

The thickness of the final film (or article) can, for example, be in the range 0.01-3.0 mm, such as 0.01-2.5 mm, 0.01-2.0 mm, 0.01-1.5 mm, 0.01-1.0 mm, 0.01-0.5 mm, 0.01-0.4 mm, 0.01-0.3 mm, 0.01-0.2 mm, 0.02-0.2 mm, 0.01-0.10 mm, 0.03-3.0 mm, 0.03-2.5 mm, 0.03-2.0 mm, 0.03-1.5 mm, 0.03-1.0 mm, 0.03-0.5 mm, 0.03-0.4 mm, 0.03-0.3 mm, 0.03-0.2 mm, 0.03-0.10 mm, 0.05-3.0 mm, 0.05-2.5 mm, 0.05-2.0 mm, 0.05-1.5 mm, 0.05-1.0 mm, 0.05-0.5 mm, 0.05-0.4 mm, 0.05-0.3 mm, 0.05-0.2 mm, 0.05-0.10 mm, 0.08-3.0 mm, 0.08-2.5 mm, 0.08-2.0 mm, 0.08-1.5 mm, 0.08-1.0 mm, 0.08-0.5 mm, 0.08-0.4 mm, 0.08-0.3 mm, 0.08-0.2 mm, 0.08-0.10 mm, 0.1-3.0 mm, 0.1-2.5 mm, 0.1-2.0 mm, 0.1-1.5 mm, 0.1-1.0 mm, 0.1-0.5 mm, 0.1-0.4 mm, 0.1-0.3 mm, 0.1-0.2 mm, 0.15-3.0 mm, 0.15-2.5 mm, 0.15-2.0 mm, 0.15-1.5 mm, 0.15-1.0 mm, 0.15-0.5 mm, 0.15-0.4 mm, 0.15-0.3 mm, 0.15-0.2 mm, 0.02-0.08 mm, 0.03-0.08 mm, or 0.05-0.08 mm. In some embodiments, the thickness of the final film (or article) can, for example, be in the range 0.05-0.08 mm for thin or disposable gloves, and in the range 0.1-3.0 mm for thick gloves.

In some embodiments, thick films are made of multiple thin layers of film to reach the desired thickness.

The thickness is suitably measured as an "average thickness", particularly for gloves, using the points of measurement described below. In some embodiments, the film thickness of a glove is less than 2 mm (e.g. from 0.01 mm to 2 mm). For example, the film thickness may be in the range of from 0.04 mm to 2 mm.

In another embodiment, the glove may have a weight of about 4 g, while it will be appreciated that higher and lower glove weights may also be obtained depending on the purpose for which the glove is to be used.

The final film (or article) can, for example, have one layer or be made from multiple layers produced by separate dipping steps. For example, the final film (or article) may comprise from 1 to 15 layers.

The final film prepared from the elastomeric film-forming composition of the invention retains the favourable feel and comfort that is closer to natural rubber film yet is free of proteins and other potential allergens (causing Type I allergy) associated with natural rubber. In some embodiments, the final film prepared from the elastomeric film-forming composition of the invention has reduced skin irritation compared to natural rubber film. For example, the final film prepared from the elastomeric film-forming composition of the invention reduces the risk of Type I allergy compared to natural rubber film. Preferably, the film prepared from the elastomeric film-forming composition of the invention avoids Type I allergy.

Where the dipped article is a glove, retaining the properties of natural rubber gloves also means that the products are easily donnable without any visible powder anti tack material. Like natural rubber gloves, the gloves of the present invention could be easily donnable without any visible powder anti tack material like talc, corn starch or calcium carbonate. In some embodiments, the gloves of the present invention could have a coating applied on the interior surface of the gloves, such as a polymeric lanlinate of acrylate or a powder to assist users in donning the gloves. Further, proper curing of the film removes tackiness, and the bonding characteristics of the carboxylic acid- or ester-grafted polychlorobutadiene makes the common coating material sufficient enough for proper donning and non-tacky effect and suitable powder free conditions. In addition, the presence of chlorine in polymer used in the elastomeric film-forming composition of the present invention acts as microbial inhibitor.

The dipped articles prepared from the elastomeric film-forming composition of the invention also possess improved physical properties. In some embodiments, the dipped articles prepared from the elastomeric film-forming composition of the invention have a higher tensile strength, a lower modulus at 300% and/or a lower modulus at 500% and a higher elongation to break when compared to other elastomeric to form a dipped articles or gloves. In some embodiments, the dipped articles prepared from the elastomeric film-forming composition of the invention have a tensile strength of greater than or equal to about 2000 psi, a modulus at 300% of about 100 to 2000 psi, a stress at 500% of about 200 to 3000 psi, and/or an elongation to break of about 400 to 1500%. For example, the elastomeric film prepared from the composition of the present invention has a tensile strength of at least about 2100 psi, a modulus at 300% of less than 660 psi, a stress at 500% of less than about 2400 psi (preferably, the stress at 500% is from about 200 psi to 1015 psi), and/or an elongation to break about 400 to 1100%. In some embodiments, the elastomeric film prepared from the composition of the present invention has a tensile strength of 2100 psi to 4000 psi, 2200 psi to 4000 psi or 2500 psi to 4000 psi. In some embodiments, the elastomeric film prepared from the composition of the present invention has a stress at 500% of 200 psi to 2400 psi, 200 psi to 1015 psi, 200 psi to 800 psi or 200 psi to 400 psi. In some embodiments, the elastomeric film prepared from the composition of the present invention has an elongation to break of greater than 520%. Preferably, the elastomeric film prepared from the composition of the present invention has an elongation to break of 520% to 1100%, greater than 650%, 650% to 1100%, 750% to 1100%, 800% to 1100%, 900% to 1100% or greater than 1000%.

The elastomeric film-forming composition of the invention can be used to form elastomeric films or dipped articles in which the softness of the film ranges from very soft to medium to very rigid by varying the amounts of the components used in the composition and the type of components used in the composition. In some embodiments, the softness of the elastomeric film or dipped article can be varied by adjusting the level of carboxylation of the polymer/copolymer, the amount and type of the second elastomer used in the composition, the amount and type of cross-linking agent or agents, and/or the amount of chlorine in the polymer/copolymer. As one example, the elastomeric film prepared from the composition of the present invention may be used to form a soft film having a tensile strength of greater than or equal to about 2100 psi, a modulus at 300% of less than or equal to about 660 psi, a stress at 500% of less than or equal to about 1015 psi, and/or an elongation to break of greater than about 800%. As another example, the elastomeric film prepared from the composition of the present invention may be used to form a soft to medium film having a tensile strength of greater than or equal to about 2100 psi, a modulus at 300% of less than or equal to about 1200 psi, a stress at 500% of less than or equal to about 2800 psi, and/or an elongation to break of about 500 to 800%. As a further example, the elastomeric film prepared from the composition of the present invention may be used to form a medium to rigid film having a tensile strength of greater than or equal to about 2100 psi, a modulus at 300% of less than about 1200 psi, a stress at 500% of less than about 2800 psi, and/or an elongation to break of about 400 to 700%.

The properties of the elastomeric film will be determined in part by the level of carboxylation of the carboxylic acid- or ester grafted polychlorobutadiene, and the amount of blending with the one or more second elastomers, and therefore, these features can be adjusted to arrive at the desired elastomeric film. This improvement may be even better when using the combination of an ionic cross-linking agent (for example a metal oxide or a metal hydroxide) and a covalent cross-linking agent (for example sulphur or a sulphur-containing vulcanising agent) as the cross-linking agents with the carboxylic acid- or ester grafted polychlorobutadiene.

For example, thinner, softer and more elastic films are produced when the carboxylic acid or ester content is in the range of about 0.01 to 5.0%, or the chlorine content is in the range of about 10 to 50%. More rigid, less elastic or more durable films are produced when the carboxylic acid or ester content is in the range of about 0.5 to 8% or the chlorine content is in the range of about 30 to 58%. When a second elastomer is used in the composition, the amount that is used will depend on the carboxylic acid or ester content and the chlorine content of the carboxylic acid- or ester-grafted polychlorobutadiene and the properties required for the resulting elastomeric film or dipped article. The amount of the second elastomer is expressed as a percentage of the polymer component of the composition on a dry basis and may be selected from within one of the following ranges: 0 to 95%, 5-95%, 0-75%, 0-65%, 5-75%, 5-65%, 10-95%, 10-75%, 10-65%, 16-95%, 15-75%, 15-65%, 20-95%, 20-75%, 20-65%, 25-95%, 25-75%, 25-65%, 30-95%, 30-75%, 30-65%, 35-95%, 35-75%, 35-65%, 40-95%, 40-75%, 40-65%. It will be appreciated that a blended composition will retain the favourable properties provided by the use of the carboxylic acid- or ester-grafted polychlorobutadiene. Preferably, the amount of the second elastomer is less than about 75%, such as 0-75%, 5-75%, 10-75%, 15-75%, 20-75%, 25-75%, 30-75%, 35-75% or 40-75%.

The desired durability of the film is determined by the end use of the article. For example, for gloves for non-surgical use, the wearing time is usually below 3 hrs, and commonly less than 2 hrs. The durability of the film can be controlled by the curing conditions. Generally, the higher the curing temperature, the more durable the elastomeric film.

The term "average thickness" in respect of the thickness of a glove (specifically the multi-layer elastomeric film forming the glove) refers to the average of three thickness measurements, taken at points along the layer of the elastomeric film. The measurements are taken at the cuff, the palm and the finger tip. When measuring the thickness of individual layers of the glove, the "average thickness" is a reference to the average thickness of that layer of film, taken at the three measurement points. This may be measured in absolute terms (in mm), or as a percentage of the full thickness of the multi-layered glove. For elastomeric articles, a similar technique using three thickness measurements can be used to determine the "average thickness".

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention is illustrated by the following examples. It is understood that one of ordinary skill in the art will understand how to vary the times and temperature of the process in accord with the article manufactured, the specific carboxylated polychloroprene copolymer or blend employed, the particular formulation ingredients selected with respect to the carboxylation level of the latex concerned.

EXAMPLES

The invention will now be described in further detail with reference to the following non-limiting examples. All testing procedures are shown in the Testing Procedures section, and the results of these tests are shown. All tables of compositions and test results are shown in the Tables section.

General Procedure

In the examples set out below, the following general procedure was utilised to produce elastomeric films, and gloves in particular. The general procedure was also used to demonstrate the impact (if any) that certain processing conditions and components of the elastomeric film forming compositions have on the quality of multilayer elastomeric films produced.

The following general procedure was followed for the all the Examples (1-10) described below.

1. Washing

The formers are subjected to pre-washing, so as to be clean of any remaining residues following removal of a glove previously made on the former. The formers are cleaned in mild acid/alkali and hot water. The formers are then dried by blowing air by blowers or air curtains or using ovens with the hot air having temperature above 105° C.

2. Coagulant Dipping

The cleaned dry former is immersed in the coagulant bath, which contains a 0-50% by weight solution of calcium nitrate. The coagulant also contains 0.1%-5.0% by weight metallic stearates, suitable wetting agents (0.001-1.0%) and antifoaming agents (0.001-1.0%).

3. Drying

The coagulant coated formers are dried in a hot air circulated oven at a temperature of about 110° C. to 130° C.

4. First Dipping Step

The former, coated with dried coagulant, is dipped into a tank of the composition for forming an elastomeric film, which contains the components specified for the given example. The composition used has a concentration of about 5 to 60% by weight, and preferably 10-40% by weight. The composition is maintained at temperature of around 20-35° C., and is constantly circulated in the tank to avoid creaming and settling of chemicals. The former is dipped into the composition for a dwell time of 5 seconds to 60 seconds.

5. Drying

The composition coated formers are gelled in a gelling oven at a temperature of about 100-300° C. and the duration of 2-300 seconds.

6. Pre-Leaching

Pre-leaching is conducted by rinsing in warm water for a short period of time. The gelled film coating on the former is pre-leached in series of tanks at ambient temperature to 55° C.

7. Second Dipping Step

Then pre-leached gelled film coating on the former is dipped into a tank of the composition for forming an elastomeric film, which contains the components specified for the given example. The composition has a concentration of about 5 to 50%, and preferably 8-35% by weight. The composition is maintained at temperature of around 10-60° C., and preferably 20-40° C., and is constantly circulated in the tank to avoid creaming and settling of chemicals. The former is dipped into the composition for a dwell time of 5-90 seconds.

8. Gelling/Pre Leaching/Beading

The product following the second dipping step is subjected to gelling and pre-leaching and beading.

The beading, drying and pre-leaching steps could be carried out in any order. The processes of beading and pre-cure leaching could be exchange depending on the quality of cuff beading.

9. Vulcanization

The beaded glove is then vulcanized at about 100° C.-150° C. for about 15-30 minutes depending upon the film thickness.

10. Post-Leaching/Lubricant/Final Drying/Stripping/Tumbling

The vulcanized glove will be post leached and lubricant dipped (optional) and stripped after final drying. Where additional curing or surface treatment is required, the gloves could be tumbled using hot air at a temperature around 40-120° C. for about 10-120 minutes.

General Formulation

The generic glove formulation is as follows:

TABLE 1

| Ingredients | Parts per Hundred Rubber (phr) - Dry basis |
|---|---|
| Carboxylic acid- or ester-grafted polychloroprene Latex* or blend** | 100-5 |
| Second elastomer | 0-95 |
| Plasticizer stabilizer | 0.5-5.0 |
| Emulsifier stabilizers | 0.5-5.0 |
| Antiozonant | 0.5-5.0 |
| pH stabilizer | 0.1-1.5 |
| Vulcanization activator | 0.5-8.0 |
| Cross-linker | 0.5-3.0 |
| Vulcanizing accelerator | 0.5-4.0 |
| Antioxidant | 0.5-3.0 |
| Opaqueness provider | 0.01-3.0 |
| Pigment | As per requirement |
| Defoamer | 0.001-2.0 |

*The carboxylic acid content is important. The effect of carboxylic content on the properties of the elastomeric film is discussed in further detail below.
**Commercially available second elastomers, such as Synthomer Type X3000 used in Examples 3 to 10 are often supplied in the form of a carboxylated nitrile butadiene rubber.

In addition to the General Formulation provided above, it will be appreciated that the following components may also be added to the formulation as necessary.

The pH stabilizers may be for example oleates, stearates or other non-ionic surfactants or potassium hydroxide, ammonium hydroxide and or sodium hydroxide.

The suitable emulsifier stabilizers may be sodium alkyl sulphates, potassium salts of resin/rosin acids or other non-ionic surfactants.

The antiozonants used may be paraffinic waxes, microcrystalline waxes and intermediate types. The vulcanization activator of metal oxides may be magnesium oxide or zinc oxide.

The cross-linker may be sulphur and/or other organic peroxides and/or cross linkable reactive monomers.

The vulcanization accelerators is chosen from mercaptobenzothiazoles and derivatives, dithiocarbamates and derivatives, sulphur donors, guanidines and its derivatives, thiourea and its derivatives and aldehyde amine reaction products.

The antioxidant may be hindered polymeric phenols or arylamines. Opaqueness provider could be titanium oxide or other minerals.

Defoamer may be naphthalene type defoamers, vegetable oil based defoamers, silicone type defoamers and like.

Carboxylic Acid or Ester Grafting of Polychlorobutadiene

The carboxylate- or ester-grafted polychlorobutadiene may be prepared using one of the various methods described in "Polymer Grafting and Cross-linking" Edited by Dr. Amit Bhattacharya, Dr. James W. Rawlins, and Dr. Paramita Ray, John Wiley & Sons, Inc., 2009, and in "Grafting: a versatile means to modify polymers: Techniques, factors and applications" Bhattacharyaa, A. and Misrab, B. N., *Progress in Polymer Science,* 2004, Volume 29, Issue 8, pages 767-814, the contents of which are incorporated herein by reference.

As one example, the carboxylate- or ester-grafted polychlorobutadiene may be prepared using the following general procedure.

A first solution containing 92-99 parts poly-2-chloro-1,3-butadiene. 1-8 parts methacrylic acid and 0.8 parts diisopropyl xanthogen disulfide is prepared. A second solution containing 3-8 parts polyvinyl alcohol (PVA) in water was also prepared. The first and second solutions were emulsified to form an oil-in-water emulsion. An amount of 90-100 parts of water was used. The redox catalyst system used was sodium sulfite and potassium persulfate, which were added as required to initiate and maintain grafting. The reaction was carried out at a temperature of 45° C. to full conversion (about 98 percent). At the end of the reaction, an emulsion containing about 0.01 part each of phenothiazine and 4-tert-butylpyrocatechol was added to stabilize against any further reaction The general procedure was used to prepare the elastomeric film forming compositions for the all the Examples (1-10) described below.

In order to produce carboxylic acid-grafted polychloroprene having levels of carboxylation of 0.01%, 1.5% and 2.5%, the method was controlled by adjusting the amount of carboxylic acid or ester used relative to the amount of polychlorobutadiene used. For 100 kg of poly-2-chloro-1,3-butadiene, the amount of methacrylic acid used was 0.02 kg, 2.925 kg and 4.875 kg, respectively (calculated at 98% conversion). The amounts of carboxylic acid or ester (or the extent of grafting or the degree of carboxylation of the polymer) may be verified by determining the amount of unreacted carboxylic acid or ester using analytical methods, and subtracting this amount from the amount of carboxylic acid or ester added.

Example 1

This Example demonstrates that single or multi-layer gloves (1-15 layers) can be made using the General Procedure outlined above. The gloves were made using the composition outlined in Table 2 below. In this Example, the carboxylic acid grafted polychloroprene copolymer (CPC) was prepared as described above, having a carboxylation level of 1.5%.

TABLE 2

| Example | 1 |
|---|---|
| Carboxylic acid-grafted polychloroprene* | 100 |
| Zinc Oxide | 1.8 |
| Sulphur | 0.6 |
| Accelerator ZDBC | 0.6 |
| TiO$_2$ | 1.0 |
| Anti oxidant | 0.6 |
| Wax | 0.5 |
| Pigment | 0.05 |
| Surfactant | 0.5 |
| pH stabilizer | 0.3 |
| Anti foam | 0.005 |

*Level of carboxylation = 1.5%

The glove produced using the above formulation and conditions stated earlier was soft and felt like glove made out of natural polyisoprene material. However the modulus and elongation were better than glove made of natural polyisoprene. The film was uniform and no weak spot or pin holes noticed. The glove thickness varied from 0.05 to 0.11 from cuff end to the finger tip.

Example 2

This Example demonstrates that single or multi-layer gloves (1-15 layers) can be made when using a different composition to that used in Example 1 above. In this Example, the carboxylic acid-grafted polychloroprene (CPC) copolymer was prepared as described above, having a carboxylation level of 2.5%. The gloves were made using the General Procedure, and using the composition outlined in Table 3 below.

TABLE 3

| Example | 2 |
|---|---|
| Carboxylic acid-grafted polychloroprene* | 100 |
| Zinc Oxide | 1.8 |
| Sulphur | 0.6 |
| ZDBC | 0.6 |
| TiO$_2$ | 1.0 |
| Anti oxidant | 0.6 |
| Wax | 0.5 |
| Pigment | 0.05 |
| Surfactant | 0.5 |
| pH stabilizer | 0.3 |
| Anti foam | 0.005 |

*Level of Carboxylation - 2.5%

The glove produced using the above formulation and conditions stated earlier was soft and felt like glove made out of natural polyisoprene material. The modulus and elongation were almost equal to that of glove made of natural polyisoprene. The film was uniform and no weak spot or pin holes were observed. The glove thickness varied from 0.05 to 0.10 from cuff end to the finger tip. The modulus of the glove was found to be higher than the gloves of Example 1 which could be due to the higher carboxylation level (2.5% against 1.5% of Example 1).

Example 3

This Example demonstrates that single or multi-layer gloves (1-15 layers) can be made when using a different composition to that used in Example 1 above. In this Example, the polymer used was CPCB (a carboxylic acid-grafted polychloroprene blend). The blend consists of 15% maximum of nitrile butadiene rubber latex (this Example used Synthomer Type X3000 which is commercially available from Synthomer, Nippon Zeon, Khumho, LG, NanTex or other material of near equivalent specifications may be used). The carboxylic acid-grafted polychloroprene was prepared as described above, having a carboxylation level of 1.5%. The composition also included higher amounts of cross-linking agents such as zinc oxide, sulphur and ZDBC, and a higher amount of the antioxidant. The gloves were made using the General Procedure, and using the composition outlined in Table 4 below.

TABLE 4

| EXAMPLE | 3 |
|---|---|
| Carboxylic acid-grafted polychloroprene * | 85 |
| Nitrile butadiene rubber latex | 15 |
| Zinc Oxide | 5 |
| Sulphur | 1 |
| Curative ZDBC | 1 |
| Titanium dioxide | 1 |
| Surfactant | 0.5 |
| Wax | 0.5 |
| Anti Oxidant | 1 |
| Pigment | 0.05 |
| pH stabilizer | 0.3 |
| Anti foam | 0.005 |

* Level of Carboxylation - 1.5%

The film was uniform and no weak spot or pin holes were observed. The glove thickness varied from 0.05 to 0.10 from cuff end to the finger tip. The modulus of the glove was found to be higher than the gloves of Example 2 which could be due to blending with nitrile butadiene rubber latex, however, the elongation was better than typical nitrile butadiene rubber products.

Example 4

This Example demonstrates that single or multi-layer gloves (1-15 layers) can be made when using a different composition to that used in Example 1 above. In this Example, the polymer used was CPCB (a carboxylic acid-grafted polychloroprene blend). The blend consists of 15% maximum of nitrile butadiene rubber latex (this Example used Synthomer Type X3000 which is commercially available from Synthomer, Nippon Zeon, Khumho, LG, NanTex or other material of near equivalent specifications may be used). The carboxylic acid-grafted polychloroprene was prepared as described above, having a carboxylation level of 2.5%. The composition also included higher amounts of cross-linking agents such as zinc oxide, sulphur and ZDBC, and a higher amount of the antioxidant. The gloves were made using the General Procedure, and using the composition outlined in Table 5 below.

TABLE 5

| EXAMPLE | 4 |
|---|---|
| Carboxylic acid-grafted polychloroprene * | 85 |
| Nitrile butadiene rubber latex | 15 |
| Zinc Oxide | 5 |
| Sulphur | 1 |
| Curative ZDBC | 1 |
| Titanium dioxide | 1 |
| Surfactant | 0.5 |
| Wax | 0.5 |
| Anti Oxidant | 1 |
| Pigment | 0.05 |
| pH stabilizer | 0.3 |
| Anti foam | 0.005 |

* Level of Carboxylation - 2.5%

The film was uniform and no weak spot or pin holes were observed. The glove thickness varied from 0.05 to 0.10 from cuff end to the finger tip. The glove found to be tougher and modulus of the glove was found to be higher than the gloves of Example 3 which could be due to blending with nitrile butadiene rubber latex and/or the higher carboxylation level of the base polymer, however, the elongation was better than typical nitrile butadiene rubber products.

Example 5

This Example demonstrates that single or multi-layer gloves (1-15 layers) can be made when using a different composition to that used in Example 1 above. In this Example, the polymer used was CPCB (a carboxylic acid-grafted polychloroprene blend). The blend consists of 15% maximum of nitrile butadiene rubber latex (this Example used Synthomer Type X3000 which is commercially available from Synthomer, Nippon Zeon, Khumho, LG, NanTex or other material of near equivalent specifications may be used). The carboxylic acid-grafted polychloroprene was prepared as described above, having a carboxylation level of 1.5%. The composition also included lower amounts of cross-linking agents such as zinc oxide, sulphur and ZDBC, and the same amount of the antioxidant as used in Examples 3 and 4. The gloves were made using the General Procedure, and using the composition outlined in Table 6 below.

TABLE 6

| EXAMPLE | 5 |
|---|---|
| Carboxylic acid-grafted polychloroprene * | 85 |
| Nitrile butadiene rubber latex | 15 |
| Zinc Oxide | 2.5 |
| Sulphur | 0.5 |
| Curative ZDBC | 0.5 |
| Titanium dioxide | 1 |
| Surfactant | 0.5 |
| Wax | 0.5 |
| Anti Oxidant | 1 |
| Pigment | 0.05 |
| pH stabilizer | 0.3 |
| Anti foam | 0.005 |

* Level of Carboxylation - 1.5%

The film was uniform and no weak spot or pin holes were observed. The glove thickness varied from 0.05 to 0.11 from cuff end to the finger tip. The glove found to be better and modulus of the glove was found to be lower than the gloves of Example 4 which could be due to the use of a lower level of chemicals, however the elongation was much better than typical nitrile butadiene rubber products.

Example 6

This Example demonstrates that single or multi-layer gloves (1-15 layers) can be made when using a different composition to that used in Example 1 above. In this Example, the polymer used was CPCB (a carboxylic acid-grafted polychloroprene blend). The blend consists of 15% maximum of nitrile butadiene rubber latex (this Example used Synthomer Type X3000 which is commercially available from Synthomer, Nippon Zeon, Khumho, LG, NanTex or other material of near equivalent specifications may be used). The carboxylic acid-grafted polychloroprene was prepared as described above, having a carboxylation level of 2.5%. The composition also included lower amounts of cross-linking agents such as zinc oxide, sulphur and ZDBC, and the same amount of the antioxidant as used in Examples 3 and 4. The gloves were made using the General Procedure, and using the composition outlined in Table 7 below.

TABLE 7

| EXAMPLE | 6 |
|---|---|
| Carboxylic acid-grafted polychloroprene * | 85 |
| Nitrile butadiene rubber latex | 15 |
| Zinc Oxide | 2.5 |
| Sulphur | 0.5 |
| Curative ZDBC | 0.5 |
| Titanium dioxide | 1 |
| Surfactant | 0.5 |
| Wax | 0.5 |
| Anti Oxidant | 1 |
| Pigment | 0.05 |
| pH stabilizer | 0.3 |
| Anti foam | 0.005 |

* Level of Carboxylation - 2.5%

The film was uniform and no weak spot or pin holes were observed. The glove thickness varied from 0.05 to 0.10 from cuff end to the finger tip. The glove found to be tougher and modulus of the glove was found to be higher than the gloves of Example 5 which could be due to higher carboxylation level of the base polymer, however, the elongation was better than typical nitrile butadiene rubber products. The strength of the gloves is better than the gloves of Example 4, where a higher level of chemicals and an equal carboxylation and blending ratio was used.

Examples 7 to 10: Experiment to Validate the Lower Limit of Carboxylation and Higher Limit of Blending In this example the validation is performed for 0.01% carboxylation and blending the composition with low cost film forming latex in amounts of up to 95%.

0.01% carboxylation was kept constant and the blending conditions were taken in stages of 30%, 45%, 75% and 95%.

These Examples demonstrate that single or multi-layer gloves (1-15 layers) can be made when using a different composition given in the table below. In these Examples, the polymer used was CPCB (a carboxylic acid-grafted polychloroprene blend). The blend consists of up to 95% of nitrile butadiene rubber latex (these Examples used Synthomer Type X3000 which is commercially available from Synthomer, Nippon Zeon, Khumho, LG, NanTex or other material of near equivalent specifications may be used). The carboxylic acid-grafted polychloroprene was prepared as described above, having a carboxylation level of 0.01%. The composition also included cross-linking agents such as zinc oxide, sulphur and ZDBC, and antioxidant as given in the table below. The gloves were made using the General Procedure, and using the composition outlined in Table 8 below.

TABLE 8

| Example | 7 | 8 | 9 | 10 |
|---|---|---|---|---|
| Carboxylic acid-grafted polychloroprene* | 25 | 55 | 70 | 5 |
| Nitrile Butadiene Rubber | 75 | 45 | 30 | 95 |
| Zinc Oxide | 2 | 3 | 4 | 1.2 |
| Sulphur | 1.5 | 1.5 | 1.5 | 1.5 |
| Curative ZDBC | 1.0 | 1.25 | 1.50 | 0.8 |
| Titanium dioxide | 2 | 2 | 2 | 2 |
| Surfactant | 0.5 | 0.5 | 0.5 | 0.5 |
| Wax | 0.5 | 0.5 | 0.5 | 0.5 |
| Anti Oxidant | 1 | 1 | 1 | 1 |
| Pigment | 0.05 | 0.05 | 0.05 | 0.05 |
| pH stabilizer | 0.3 | 0.3 | 0.3 | 0.3 |
| Antifoam | 0.005 | 0.005 | 0.005 | 0.005 |

*Level of Carboxylation - 0.01%

The gloves made from the above compositions had a uniform film and no weak spots or pin holes were observed. The glove thickness varied from 0.05 to 0.10 from cuff end to the finger tip.

Example 7

The resulting glove was tough and almost like nitrile gloves with minimal elasticity. However, it is still better than the regular nitrile gloves by feel and softness due to the presence of carboxylated polychlroroprene.

Example 8

The gloves produced were softer than the gloves of Example 7.

Example 9

The resulting glove was soft and had a stretchability that was better than the gloves of Examples 7 and 8.

Example 10

The resulting glove was tough and almost like nitrile gloves with minimal elasticity. Such gloves may be suitable for low cost applications where comfort is not a crucial factor. However, it will be appreciated that the formulation could be further modified by reducing the amount or type of cross-linking agents to make a softer and/or more stretchable glove.

TEST PROCEDURES

Figure 2A:
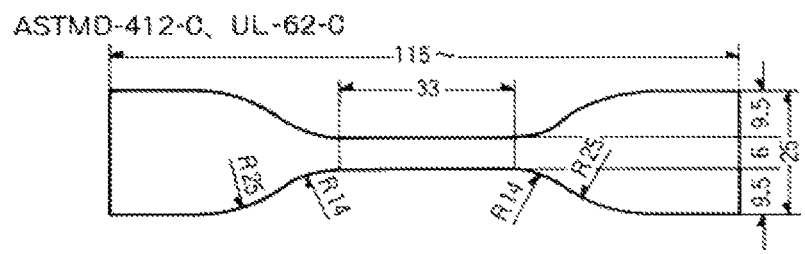
FIG. 2A is a schematic diagram showing an ASTM D412 Type C sample cutting die.
Figure 2B:
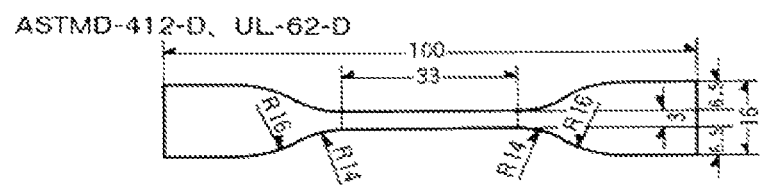
FIG. 2B is a schematic diagram showing an ASTM D412 Type D sample cutting die. The ASTM D412 Type C and ASTM D412 Type D sample cutting dies may be used to prepare test specimens for measuring tensile strength, stress at 300% and 500% modulus and elongation to break according to the testing procedures set forth in the ASTM D 412-06a (2013) standard. This standard is available from ASTM International, and details the standard specifications and testing standards used for testing vulcanized rubber and Thermoplastic elastomers. These tests can be applied to multilayer films and gloves (such as examination and surgical gloves for medical applications).

For all of the Examples, the following testing techniques were used.
General Testing Procedures Tensile strength, stress at 300% and 500% modulus and elongation to break were measured by testing procedures conducted in accordance with ASTM D 412-06a (2013). This standard is available from ASTM International, and details the standard specifications and testing standards used for testing vulcanized rubber and Thermoplastic elastomers. These tests can be applied to multilayer films and gloves (such as examination and surgical gloves for medical applications). FIG. 2A is a schematic diagram showing an ASTM D412 Type C sample cutting die. FIG. 2B is a schematic diagram showing an ASTM D412 Type D sample cutting die. The dies are used to prepare test specimens for testing according to the ASTM D 412-06a standard.
Results The elastomeric films prepared using the elastomeric film-forming compositions of Examples 1 to 6 were tested, and the following properties of the elastomeric films were measured:
  Modulus at 300%
  Modulus at 500%
  Tensile strength (Psi); and
  Elongation %.
The results of these measurements are shown in Table 9.

TABLE 9

| | Example | | | | | |
|---|---|---|---|---|---|---|
| | 1 | 2 | 3 | 4 | 5 | 6 |
| % Carboxylation | 1.5 | 2.5 | 1.5 | 2.5 | 1.5 | 2.5 |
| Polymer# | CPC | CPC | CPCB | CPCB | CPCB | CPCB |
| Curatives* | Low | Low | High | High | Low | Low |
| Modulus at 300% | 150 | 270 | 430 | 605 | 390 | 550 |
| Modulus at 500% | 220 | 350 | 840 | 890 | 650 | 835 |
| Tensile strength Psi | 2900 | 3050 | 2830 | 2900 | 2925 | 3145 |
| Elongation % | 1050 | 925 | 785 | 760 | 820 | 775 |

CPC refers to a carboxylic acid-grafted polychloroprene having the specified % carboxylation. CPCB refers to a blend containing a carboxylic acid-grafted polychloroprene having the specified % carboxylation and a second elastomer as described in Examples 3 to 6 above.

TABLE 10

| | Example | | | |
|---|---|---|---|---|
| | 7 | 8 | 9 | 10 |
| % Carboxylation | 0.01 | 0.01 | 0.01 | 0.01 |
| CPC# phr | 25 | 55 | 70 | 5 |
| Nitrile Butadiene Rubber phr | 75 | 45 | 30 | 95 |
| Modulus at 300% | 610 | 335 | 330 | 650 |

TABLE 10-continued

| | Example | | | |
|---|---|---|---|---|
| | 7 | 8 | 9 | 10 |
| Modulus at 500% | 2030 | 800 | 730 | 2320 |
| Tensile strength Psi | 3190 | 2320 | 2180 | 3340 |
| Elongation % | 550 | 630 | 700 | 530 |

CPC refers to a carboxylic acid-grafted polychloroprene having the specified % carboxylation.

By comparing the values obtained for each of these compositions, the following general conclusions can be made:

1. The lower the degree of carboxylation of the polymer, the higher the elasticity of the film. As shown in Table 9 above, the elongation % is higher in Examples 1, 3 and 5 which used a polymer having a carboxylation level of 1.5% when compared with Examples 2, 4 and 6 which used a polymer having a carboxylation level of 2.5%. It follows that the higher the carboxylation level, the higher the modulus at 300%, the modulus at 500%, and the tensile strength, but the film will have a lower elongation %.

2. The lower the degree of carboxylation of the polymer, the lower the modulus of the film. As shown in Table 9 above, the modulus is lower in Examples 1, 3 and 5 which used a polymer having a carboxylation level of 1.5% when compared with Examples 2, 4 and 6 which used a polymer having a carboxylation level of 2.5%.

3. The higher level of cross-linking agents used in Examples 3 and 4 does not have significant effect on tensile strength than the lower level of cross-linking agents used in Examples 5 and 6. However, the modulus values for Examples 3 and 4 are marginally higher and the elongation is marginally lower when compared to Examples 5 and 6. This result suggests that increased amounts of cross-linking agents does not have much impact.

4. By comparison of the modulus values of Examples 1 and 2 against the modulus values of Examples 3-6, it can be found that when the carboxylic acid-grafted polychloroprene is used, the modulus of the elastomeric film is lower than when the blend containing a carboxylic acid-grafted polychloroprene is used. However, it will be appreciated that articles prepared using the blend containing a carboxylic acid-grafted polychloroprene could be used in selected applications.

5. Examples 5 and 6 were made with equal levels of crosslinking agents (2.5 phr ZnO, 0.5 phr sulphur and 0.5 phr ZDBC) with the blending ratio of 15% by weight. However the carboxylation levels of Examples 5 and 6 were 1.5 and 2.5%, respectively. It is evident from FIG. 1, that even with limited blending (i.e. a lower amount of the second elastomer), a higher carboxylation level results in a higher modulus at 300%, modulus at 500%, and tensile strength, but a lower elongation %.

6. The total % chemical consumption in Examples 1 & 2 is less when compared to the conventional curing system used for polychloroprene polymers. In particular, the total % chemical consumption of metal oxide is only 1.8%, while in the conventional curing system used for polychloroprene polymers, the total % chemical consumption of metal oxide varies from 6 to 10%, which is approximately 3 to 5 times more. In addition, curing could be achieved at 100-130° C. for an oven residence time of 15-30 minutes. The reduction in the amount of zinc oxide, combined with the temperature and duration required for curing provides numerous environmental advantages.

7. Examples 9, 8, 7 and 10 were made with a carboxylation level of 0.01%, however, the amount of the second elastomer is 30, 45, 75 and 95 respectively. The ZnO level was 4 phr, 3 phr, 2 phr and 1.2 phr (for Examples 9, 8, 7 and 10, respectively), the sulphur level was 1.5 phr, and the ZDBC level was 1.5 phr, 1.25 phr, 1.0 phr, and 0.8 phr (for Examples 9, 8, 7 and 10, respectively). With the increasing amount of the second elastomer, the modulus at 300%, modulus at 500%, and tensile strength increased, while the elongation % decreased.

8. Of Examples 1 to 10, Example 1 gave the lowest modulus (150 psi) and highest elongation (1050%).

Validating the Limits of Lower Carboxylation Level and Higher Blending (Table 10)

The lowest carboxylation level and highest blending level provide suitable gloves despite that the product is not as soft as those of Examples 1 to 6.

The gloves of Example 7, 8, 9 and 10 will pass ASTM specification for medical gloves made using polychloroprene material, hence the limits are validated to make the gloves.

In the case of examples 7, 8, 9 and 10, it has been found that the glove becomes softer as the amount of carboxylic acid-grafted polychloroprene (having a percent carboxylation of 0.01) increases, in other words the modulus values and tensile values increase as the amount of carboxylic acid-grafted polychloroprene is reduced and the nitrile butadiene rubber content increases. The elongation increases as the amount of carboxylic acid-grafting increases.

The foregoing description and examples relate only to preferred embodiments of the present invention and numerous changes and modifications may be made therein without departing from the spirit and scope of the invention as defined in the following claims.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Items

The present invention relates to the following items:

1. An elastomeric film-forming composition comprising:
   a carboxylic acid- or ester-grafted polychlorobutadiene, and
   one or more cross-linking agents.
2. The composition of item 1, wherein the chlorobutadiene is selected from the group consisting of 2-chloro-1,3-butadiene, 2,3-dichloro-1,3-butadiene and combinations thereof.
3. The composition of item 1 or 2, wherein the carboxylic acid or ester is an ethylenically unsaturated carboxylic acid or ester having the formula:

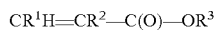

or

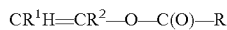

wherein
$R^1$ is hydrogen, an alkyl radical containing 1 to 4 carbon atoms, —C(O)—OR$^4$ or —R$^5$—C(O)—OH, wherein R$^4$ is hydrogen or an alkyl radical containing 1 to 4 carbon atoms and R$^5$ is an alkyl radical containing 1 to 4 carbon atoms;
$R^2$ is hydrogen, an alkyl radical containing 1 to 4 carbon atoms, or a carboxymethyl radical;
$R^3$ is hydrogen, an alkyl radical containing 1 to 4 carbon atoms, or —R$^6$O—C(O)—CR$^7$=CR$^8$, wherein R$^6$ is an alkyl radical containing 1 to 4 carbon atoms, and R$^7$ and R$^8$ are each independently hydrogen or an alkyl radical containing 1 to 4 carbon atoms; and
cis or trans isomers thereof.

4. The composition of any one of items 1 to 3, wherein the carboxylic acid or ester is selected from the group consisting of acrylic acid, methacrylic acid, crotonic acid, fumaric acid, maleic acid, citraconic acid, glutaconic acid, vinyl acetate, methyl acrylate, methacrylate ester, ethylenediol dimethacrylate, butanediol dimethacrylate, methymethacrylate, butylmethacrylate, glacialmethacrylic acid and combinations thereof.
5. The composition of any one of items 1 to 4, wherein the carboxylic acid- or ester-grafted polychlorobutadiene contains the carboxylic acid or ester in an amount of from 0.01% to 8% by weight of the chlorobutadiene units present in the polymer.
6. The composition of any one of items 1 to 5, wherein the polymer comprises from 10 to 60% or 10 to 58% chlorine by weight of the chlorobutadiene units present in the polymer.
7. The composition of any one of items 1 to 6, wherein the concentration of the total solids in the composition is between 5-60% by weight of the composition.
8. The composition of any one of items 1 to 7, wherein the cross-linking agent is selected from the group consisting of carbamates, thiocarbamates, thiurams, thiourea, thiazoles, guanidines, aldehyde/amine-based accelerators, ionic cross-linking agents, organic and inorganic metal oxides, organic and inorganic metal hydroxides organic and inorganic peroxides, covalent cross-linking agents, sulphur, crosslinking monomers, reactive oligomers, polyisocyanate oligomers, functional crosslinkable polymers; derivatives of ethylene glycol di(meth)acrylate, derivatives of methylenebisacrylamide, formaldehyde-free crosslinking agents, divinylbenzene, divinylether, diallyl phthalate, divinylsulfone and and combinations thereof.
9. The composition of item 8, wherein the cross-linking agent comprises an ionic cross-linking agent and a covalent cross-linking agent.
10. The composition according to item 9, wherein the ionic cross-linking agent is a metal oxide or metal hydroxide.
11. The composition according to item 10, wherein the metal oxide or metal hydroxide is selected from one or a mixture of agents from the group consisting of lead oxide, magnesium oxide, barium oxide, zinc oxide, manganese oxide, copper oxide, nickel oxide, aluminium oxide, zinc hydroxide, magnesium hydroxide, barium hydroxide, manganese hydroxide, copper hydroxide, aluminium hydroxide and nickel hydroxide.
12. The composition according to item 9, wherein the covalent cross-linking agent is sulphur or a sulphur-containing vulcanising agent.
13. The composition according to any one of items 1 to 12, wherein the amount of cross-linking agent in the composition is in the range 0.5-15.0 phr, 1.0-15.0 phr, 1.5-15.0 phr, 0.5-13.0 phr, 1.0-13.0 phr, 1.5-13.0 phr, 0.5-11.0 phr, 1.0-11.0 phr, 1.5-11.0 phr, 0.5-10.0 phr, 1.0-10.0 phr, 1.5-10.0 phr, 0.5-8.0 phr, 1.0-8.0 phr, 1.5-8.0 phr, 0.5-7.0 phr, 1.0-7.0 phr, 1.5-7.0 phr, 2.0-8.0 phr, 2.5-10.0 phr, 5.0-10.0 phr, 3.0-7.0 phr, 3.0-6.0 phr, 4.0-7.0 phr, 4.0-6.0 phr, 4.0-5.0 phr, 2.0-5.0 phr, 2.0-4.0 phr, 3.0-4.0 phr, 0.01-3.5 phr, 0.01-3.0 phr, 0.01-2.0 phr, 0.01-1.5 phr, 0.01-1.0 phr or 0.01-0.5 phr.

14. The composition of item 10 or 11, wherein the amount of metal oxide or metal hydroxide cross-linking agent in the composition is in the range 1.0-10.0 phr, 2.0-8.0 phr, 2.5-10.0 phr, 5.0-10.0 phr, 3.0-7.0 phr, 3.0-6.0 phr, 4.0-7.0 phr, 4.0-6.0 phr, 4.0-5.0 phr, 2.0-5.0 phr, 2.0-4.0 phr or 3.0-4.0 phr 15. The composition according to item 12, wherein the amount of sulphur or sulphur-containing vulcanising agent in the composition is in the range 0.01-3.5 phr, 0.01-3.0 phr, 0.01-2.0 phr, 0.01-1.5 phr, 0.01-1.0 phr or 0.01-0.5 phr.

16. The composition of any one of items 1 to 13, wherein the composition further comprises a second elastomer selected from the group consisting of nitrile rubber, styrene butadiene rubber, butyl rubber, polyisoprene, polychloroprene, polybutadiene, polyvinylchloride, polyurethane, styrene diblock copolymers, styrene triblock copolymers, acrylic polymers and mixtures thereof.

17. The composition of item 16, wherein the second elastomer is carboxylated, non-carboxylated or a mixture of carboxylated and non-carboxylated elastomers.

18. The composition of item 16 or 17, wherein the second elastomer is present in an amount of 0-95%, 5-95%, 0-75%, 5-75%, 0-65%, 5-65%, 0-50%, 5-50%, 10-95%, 10-75%, 10-65%, 15-95%, 15-75%, 15-65%, 20-95%, 20-75%, 20-65%, 25-95%, 25-75%, 25-65%, 30-95%, 30-75%, 30-65%, 35-95%, 35-75%, 35-65%, 40-95%, 40-75%, 40-65%, 50-95%, 50-75%, 50-60%, 50-65%, 60-65%, 60-75%, 60-80%, 60-95%, 70-90%, 70-95%, 80-95%, 1-5%, 5-10%, 10-15%, 15-20%, 20-25%, 25-30%, 30-35%, 35-40%, or 40-50% by weight of the polymer component of the composition.

19. A dipped article made from an elastomeric film comprising:
at least one layer of a cured composition of
a carboxylic acid- or ester-grafted polychlorobutadiene, and
one or more cross-linking agents.

20. A dipped article made from the elastomeric film-forming composition of any one of items 1 to 18.

21. The dipped article of item 19 or 20, wherein the article is a glove.

22. The dipped article of any one of items 19 to 21, wherein the average thickness of the elastomeric film is between about 0.01 mm to about 3 mm.

23. The dipped article of any one of items 19 to 22, wherein the elastomeric film comprises from 1 to 15 layers, and each layer is produced by a separate dipping step.

24. A glove comprising at least one layer of elastomeric film comprising: a carboxylic acid- or ester-grafted polychlorobutadiene, which is cross-linked with one or more cross-linking agents.

25. The glove of item 24, having a tensile strength of greater than or equal to about 2000 psi, a modulus at 300% of about 100 to 2000 psi, a stress at 500% of about 200 to 3000 psi, and/or an elongation to break of about 400 to 1500%.

26. The glove of item 24 or 25, wherein the chlorobutadiene is selected from the group consisting of 2-chloro-1,3-butadiene, 2,3-dichloro-1,3-butadiene and combinations thereof.

27. The glove of any one of items 24 to 26, wherein the carboxylic acid or ester is an ethylenically unsaturated carboxylic acid or ester having the formula:

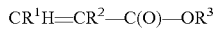

or

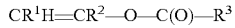

wherein
$R^1$ is hydrogen, an alkyl radical containing 1 to 4 carbon atoms, —C(O)—OR$^4$ or —R$^5$—C(O)—OH, wherein $R^4$ is hydrogen or an alkyl radical containing 1 to 4 carbon atoms and $R^5$ is an alkyl radical containing 1 to 4 carbon atoms;
$R^2$ is hydrogen, an alkyl radical containing 1 to 4 carbon atoms, or a carboxymethyl radical;
$R^3$ is hydrogen, an alkyl radical containing 1 to 4 carbon atoms, or —R$^6$O—C(O)—CR$^7$=CR$^8$, wherein $R^6$ is an alkyl radical containing 1 to 4 carbon atoms, and $R^7$ and $R^8$ are each independently hydrogen or an alkyl radical containing 1 to 4 carbon atoms; and
cis or trans isomers thereof.

28. The glove of any one of items 24 to 27, wherein the carboxylic acid or ester is selected from the group consisting of acrylic acid, methacrylic acid, crotonic acid, fumaric acid, maleic acid, citraconic acid, glutaconic acid, vinyl acetate, methyl acrylate, methacrylate ester, ethylenediol dimethacrylate, butanediol dimethacrylate, methymethacrylate, butylmethacrylate, glacialmethacrylic acid and combinations thereof.

29. The glove of any one of items 24 to 28, wherein the carboxylic acid- or ester-grafted polychlorobutadiene contains the carboxylic acid or ester in an amount of from 0.01% to 8% by weight of the chlorobutadiene units present in the polymer.

30. The glove of any one of items 24 to 29, wherein the polymer comprises from 10 to 60% or 10 to 58% chlorine by weight of the chlorobutadiene units present in the polymer.

31. The glove of any one of items 24 to 30, wherein the cross-linking agent comprises an ionic cross-linking agent and a covalent cross-linking agent.

32. The glove according to item 31, wherein the ionic cross-linking agent is a metal oxide or metal hydroxide.

33. The glove according to item 32, wherein the metal oxide or metal hydroxide is selected from one or a mixture of agents from the group consisting of lead oxide, magnesium oxide, barium oxide, zinc oxide, manganese oxide, copper oxide, nickel oxide, aluminium oxide, zinc hydroxide, magnesium hydroxide, barium hydroxide, manganese hydroxide, copper hydroxide, aluminium hydroxide and nickel hydroxide.

34. The glove according to item 31, wherein the covalent cross-linking agent is sulphur or a sulphur-containing vulcanising agent.

35. The glove of item 32 or 33, wherein the amount of metal-oxide or metal hydroxide cross-linking agent in the composition is in the range 1.0-10.0 phr, 2.0-8.0 phr, 2.5-10.0 phr, 5.0-10.0 phr, 3.0-7.0 phr, 3.0-6.0 phr, 4.0-7.0 phr, 4.0-6.0 phr, 4.0-5.0 phr, 2.0-5.0 phr, 2.0-4.0 phr, 3.0-4.0 phr 36. The glove of item 34, wherein the amount of sulphur or sulphur-containing vulcanising agent is in the range 0.0-3.5 phr, 0.01-3.5 phr, 0.01-3.0 phr, 0.01-2.0 phr, 0.01-1.5 phr, 0.01-1.0 phr or 0.01-0.5 phr 37. The glove of any one of items 24 to 36, wherein the elastomeric film further comprises a second elastomer selected from the group consisting of nitrile rubber, styrene butadiene rubber, butyl rubber, polyisoprene, polychloroprene, polybutadiene, polyvinylchloride, polyurethane, styrene diblock copolymers, styrene triblock copolymers, acrylic polymers and mixtures thereof.

38. The glove of item 37, wherein the second elastomer is carboxylated, non-carboxylated or a mixture of carboxylated and non-carboxylated elastomers.

39. The glove of item 37 or 38, wherein the second elastomer is present in an amount of from 0% up to 95% by weight of the polymer component of the composition.

40. The glove of any one of items 24 to 39, wherein the average thickness of the elastomeric film is between about 0.01 mm to about 3 mm.

41. The glove of any one of items 24 to 40, wherein the glove comprises from 1 to 15 layers ofelastomeric film composition, and each layer is produced by a separate dipping step.

42. A method of manufacturing an elastomeric film comprising the steps of:
 (i) dipping a former into a composition of any one of items 1 to 18 to produce a layer of elastomeric film-forming composition on the former, and
 (ii) drying and curing the elastomeric film-forming composition.

43. The method of item 42, further comprising, prior to step (i), the steps of:
 (a) dipping the former into a coagulant, followed by
 (b) drying or partially drying the coagulant-dipped former.

44. A method of manufacturing an elastomeric film comprising the steps of:
 (i) dipping a former into a composition of any one of items 1 to 18 to produce a layer of elastomeric film-forming composition on the former,
 (ii) drying the elastomeric film-forming composition, and
 (v) drying and curing the layered elastomeric film.

45. A multiple-coating method of manufacturing a layered elastomeric film comprising the steps of:
 (i) dipping a former into a composition of any one of items 1 to 18 to produce a layer of elastomeric film-forming composition on the former,
 (ii) drying the elastomeric film-forming composition,
 (iii) dipping the former into a composition of any one of items 1 to 18 to produce a further layer of elastomeric film-forming composition on the former,
 (iv) optionally repeating the drying step (ii) and the further dipping step (iii), and
 (v) drying and curing the layered elastomeric film.

46. The method of item 44 or 45, further comprising, prior to step (i), the steps of:
 (a) dipping the former into a coagulant, followed by
 (b) drying or partially drying the coagulant-dipped former.

47. The method of any one of items 42 to 46, wherein the drying step and the dipping step are repeated to produce a film having from 2 to 15 layers.

48. The method of any one of items 42 to 47, wherein the film has between 1-15, 2-6, 2-5, 1-4, 2-3, or 1-3 layers.

49. The method of any one of items 42 to 48, wherein the former is a hand-shaped mould, and the layered elastomeric film is in the shape of a glove.

50. The elastomeric film produced by the method of any one of items 42 to 49.

51. Use of an elastomeric film-forming composition comprising:
 a carboxylic acid- or ester-grafted polychlorobutadiene, and
 one or more cross-linking agents,
in the manufacture of a glove.

The invention claimed is:

1. An elastomeric film-forming composition comprising:
 (a) a polymer component comprising a carboxylic acid- or ester-grafted polychlorobutadiene, and
 (b) one or more cross-linking agents,
 wherein the carboxylic acid or ester-grafted polychlorobutadiene contains carboxylic acid or ester grafting in an amount of from 0.01% to 8% by weight of chlorobutadiene units present in the carboxylic acid or ester-grafted polychlorobutadiene.

2. The composition of claim 1, wherein the polychlorobutadiene is selected from the group consisting of a polymer of 2-chloro-1,3-butadiene, a polymer of 2,3-dichloro-1,3-butadiene and copolymers comprising 2-chloro-1,3-butadiene and 2,3-dichloro-1,3-butadiene.

3. The composition of claim 1, wherein the carboxylic acid or ester-grafted polychlorobutadiene comprises from 10 to 60% chlorine by weight of the chlorobutadiene units present in the carboxylic acid or ester-grafted polychlorobutadiene.

4. The composition of claim 1, wherein a concentration of total solids in the composition is between 5-60% by weight of the composition.

5. The composition of claim 1, wherein the cross-linking agent is selected from the group consisting of carbamates, thiocarbamates, thiurams, thiourea, thiazoles, guanidines, aldehyde/amine-based accelerators, ionic cross-linking agents, organic and inorganic metal oxides, organic and inorganic metal hydroxides, organic and inorganic peroxides, covalent cross-linking agents, sulphur, crosslinking monomers, reactive oligomers, polyisocyanate oligomers, functional crosslinkable polymers; derivatives of ethylene glycol di(meth)acrylate, derivatives of methylenebisacrylamide, formaldehyde-free crosslinking agents, divinylbenzene, divinylether, diallyl phthalate, divinylsulfone and combinations thereof.

6. The composition of claim 5, wherein the cross-linking agent comprises an ionic cross-linking agent and a covalent cross-linking agent.

7. The composition of claim 6, wherein the ionic cross-linking agent is a metal oxide or metal hydroxide.

8. The composition of claim 6, wherein the covalent cross-linking agent is at least one of (i) sulphur and (ii) a sulphur-containing vulcanising agent.

9. The composition according to claim 1, wherein an amount of cross-linking agent in the composition is in the range of 0.5-15.0 phr.

10. The composition of claim 1, wherein the polymer component further comprises a second elastomer selected from the group consisting of nitrile rubber, styrene butadiene rubber, butyl rubber, polyisoprene, polychloroprene, polybutadiene, polyvinylchloride, polyurethane, styrene diblock copolymers, styrene triblock copolymers, acrylic polymers and mixtures thereof.

11. The composition of claim 10, wherein the second elastomer is carboxylated, non-carboxylated or a mixture of carboxylated and non-carboxylated elastomers.

12. The composition of claim 10, wherein the second elastomer is present in an amount of 0-95% by weight of the polymer component of the composition.

13. The composition of claim 1, wherein the carboxylic acid or ester-grafted polychlorobutadiene contains carboxylic acid or ester grafting in an amount of from about 0.5% to about 5% by weight of the chlorobutadiene units present in the carboxylic acid or ester-grafted polychlorobutadiene.

14. A dipped article made from the elastomeric film-forming composition of claim 1.

15. The dipped article of claim 14, wherein the article is a glove.

16. The dipped article of claim 14, wherein an average thickness of the elastomeric film is between about 0.01 mm to about 3 mm.

17. The dipped article of claim 14, wherein an average thickness of the elastomeric film is between about 0.01 mm to about 5 mm.

18. The dipped article of claim 14, wherein the elastomeric film comprises from 1 to 15 layers, and each layer is produced by a separate dipping step.

19. The dipped article of claim 14, wherein the dipped article has at least one of (i) a tensile strength of greater than or equal to about 2000 psi, (ii) a modulus at 300% of about 100 to 2000 psi, (iii) a stress at 500% of about 200 to 3000 psi, and (iv) an elongation to break of about 400 to 1500%.

20. A method of manufacturing an elastomeric film comprising the steps of:
  (i) dipping a former into the elastomeric film-forming composition of claim 1, and
  (ii) drying and curing the elastomeric film-forming composition.

21. The method of claim 20 wherein, prior to step (i), the method comprises the steps of:
  dipping the former into a coagulant, followed by
  drying or partially drying the coagulant-dipped former.

22. The method of claim 20, wherein, betweem steps (i) and (ii), the method comprises the steps of:
  (ia) drying the layer produced in step (i), and
  (ib) dipping the former into a second elastomeric film-forming composition comprising (a) a carboxylic acid- or ester-grafted polychlorobutadiene, and (b) one or more cross-linking agents, to produce a further layer of elastomeric film-forming composition on the former.

23. The method of claim 20, wherein the drying step and the dipping step are repeated to produce a film having from 2 to 15 layers.

24. The method of claim 20, wherein the former is a hand-shaped mould, and the layered elastomeric film is in the shape of a glove.

25. The elastomeric film produced by the method of claim 20.

26. A method of manufacturing a glove, comprising the use of the elastomeric film-forming composition of claim 1.

27. The composition of claim 1, wherein the concentration of the total solids in the composition is between 5-40% by weight of the composition.

28. The composition of claim 1, wherein the concentration of the total solids in the composition is between 5-30% by weight of the composition.

29. The composition of claim 1, wherein the carboxylic acid or ester-grafted polychlorobutadiene contains carboxylic acid or ester grafting in an amount of from 0.01% to 4% by weight of the chlorobutadiene units present in the polymer.

30. The composition of claim 1, wherein the carboxylic acid or ester-grafted polychlorobutadiene is a polychlorobutadiene polymer containing no carboxylic acid or ester groups in the main chain and wherein the carboxylic acid or ester is grafted onto the main chain.

31. The dipped article of claim 14, wherein the carboxylic acid or ester-grafted polychlorobutadiene present in the elastomeric film-forming composition from which the dipped article is made contains carboxylic acid or ester grafting in an amount of from 0.01% to 4% by weight of the chlorobutadiene units present in the polymer.

32. The dipped article claim 14, wherein the carboxylic acid or ester-grafted polychlorobutadiene present in the elastomeric film-forming composition from which the dipped article is made comprises a polychlorobutadiene polymer containing no carboxylic acid or ester groups in the main chain and wherein the carboxylic acid or ester is grafted onto the main chain.

33. The method of claim 20, wherein the carboxylic acid or ester-grafted polychlorobutadiene present in the elastomeric film-forming composition into which the former is dipped contains carboxylic acid or ester grafting in an amount of from 0.01% to 4% by weight of the chlorobutadiene units present in the polymer.

34. The method of claim 20, wherein the carboxylic acid or ester-grafted polychlorobutadiene present in the elastomeric film-forming composition into which the former is dipped comprises a polychlorobutadiene polymer containing no carboxylic acid or ester groups in the main chain and the carboxylic acid or ester grafted onto the main chain.

35. The method of claim 20, wherein the total solids content of the elastomeric film-forming composition into which the former is dipped is between 5 and 60% by weight.

36. The method of claim 20, wherein the total solids content of the elastomeric film-forming composition into which the former is dipped is between 5 and 40% by weight.

37. The method of claim 20, wherein the total solids content of the elastomeric film-forming composition into which the former is dipped is between 5 and 30% by weight.

* * * * *